(12) United States Patent
Kruglick

(10) Patent No.: US 9,388,379 B2
(45) Date of Patent: Jul. 12, 2016

(54) DYNAMICALLY ALTERABLE CELL SUPPORT

(75) Inventor: Ezekiel Kruglick, Poway, CA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 111 days.

(21) Appl. No.: 13/202,565

(22) PCT Filed: Feb. 25, 2011

(86) PCT No.: PCT/US2011/026346
§ 371 (c)(1),
(2), (4) Date: Aug. 19, 2011

(87) PCT Pub. No.: WO2012/115658
PCT Pub. Date: Aug. 30, 2012

(65) Prior Publication Data
US 2013/0323841 A1 Dec. 5, 2013

(51) Int. Cl.
*C12N 5/00* (2006.01)
*C12M 1/12* (2006.01)

(52) U.S. Cl.
CPC ............ *C12N 5/0068* (2013.01); *C12M 25/00* (2013.01); *Y10T 29/49863* (2015.01)

(58) Field of Classification Search
CPC ............ C12N 5/0068; C12N 2533/52; C12N 2533/30; C12M 25/00; C12M 25/02; C12M 25/14; C12M 35/04; C12M 23/20; Y10T 29/49863
USPC .............. 435/299.1, 402, 289.1, 395; 29/446
See application file for complete search history.

(56) References Cited

U.S. PATENT DOCUMENTS

| | | | | | |
|---|---|---|---|---|---|
| 4,343,904 | A | * | 8/1982 | Birch et al. | 435/395 |
| 4,839,280 | A | * | 6/1989 | Banes | 435/305.2 |
| 6,048,723 | A | * | 4/2000 | Banes | C12M 23/12 |
| | | | | | 435/288.3 |
| 6,576,458 | B1 | | 6/2003 | Sarem et al. | |
| 6,586,235 | B1 | * | 7/2003 | Banes | C12M 23/10 |
| | | | | | 435/293.1 |
| 8,058,057 | B2 | * | 11/2011 | Cattadoris | B01F 11/0065 |
| | | | | | 366/275 |
| 2004/0219668 | A1 | | 11/2004 | Frei et al. | |
| 2006/0270023 | A1 | * | 11/2006 | LeDuc et al. | 435/289.1 |

FOREIGN PATENT DOCUMENTS

| | | | | |
|---|---|---|---|---|
| DE | CA 2387549 A1 | * | 2/2001 | ............ C12M 23/24 |
| SU | 1691391 | | 11/1991 | |
| WO | 2004090091 | | 10/2004 | |

OTHER PUBLICATIONS

International Preliminary Report on Patentability for Intl. Pat. Appln. No. PCT/US2011/026346, mailed on Sep. 6, 2013, 8 pp.

(Continued)

*Primary Examiner* — William H Beisner
*Assistant Examiner* — Danielle Henkel
(74) *Attorney, Agent, or Firm* — Foley & Lardner LLP

(57) ABSTRACT

A dynamically alterable cell support may be altered at a large scale to induce mechanical removal of adherent cells in culture without the use of a removal solution. For example, adherent cells may be cultured on an elastic support with one or more textured surface regions and removed by expansion/contraction of the support. Mechanical removal of adherent cells may reduce or minimize damage to cell surface markers, cellular morphology, and/or cellular physiology associated with the detachment and resuspension of cultured adherent cells.

16 Claims, 22 Drawing Sheets

(56) References Cited

OTHER PUBLICATIONS

International Search Report and Written Opinion, issued in International Patent Application No. PCT/US2011/026346, mailed Apr. 27, 2011, 10 pages.
Reilly, G. C. et al., "Intrinsic extracellular matrix properties regulate stem cell differentiation," Journal of Biomechanics, Sep. 2009, pp. 1-8.
Deval, J. et al., "Reconfigurable hydrophobic/hydrophilic surfaces in microelectromechanical systems (MEMS)," J. Micromech. Microeng., 2004, pp. 91-95, vol. 14.
Zellwerk Gmbh, "Removing cells from Sponceram carrier discs in the technology," Application Note, 2009, 2 pages.
Abbott, A., "Biology's new dimension," Nature, 424, pp. 870-872 (Aug. 21, 2003).
Cooke, M. J., et al., "Enhanced cell attachment using a novel cell culture surface presenting functional domains from extracellular matrix proteins," Cytotechnology, vol. 56, pp. 71-79 (Jan. 25, 2008).
Korin N., et al., "Design of well and groove microchannel bioreactors for cell cufture," Biotechnol. Bioeng., vol. 102, No. 4, pp. 1222-1230 (Mar. 1, 2009).
Sato K., and Kitamori T., "Development of Fundamental Technologies for Micro Bioreactors." Adv Biochem Engin Biotechnol., vol. 119, pp. 251-265 (2010).

* cited by examiner

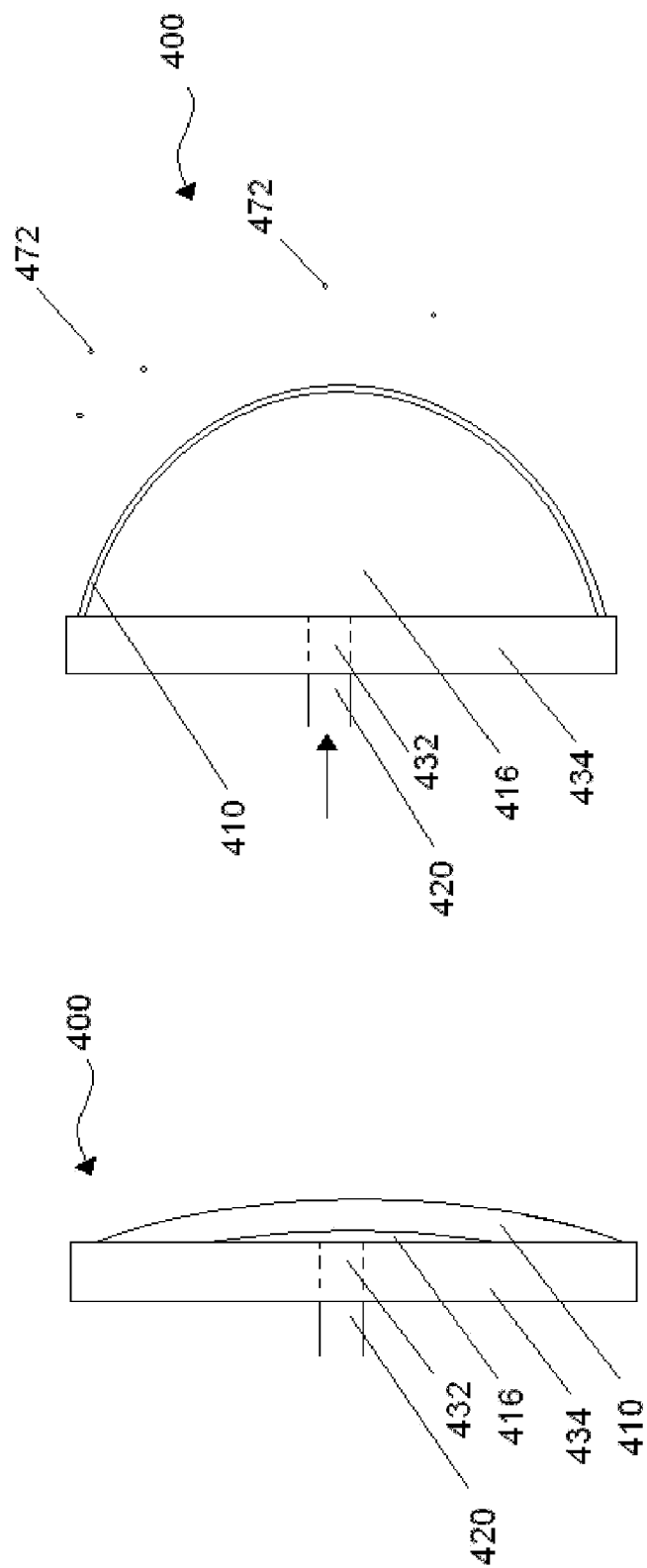

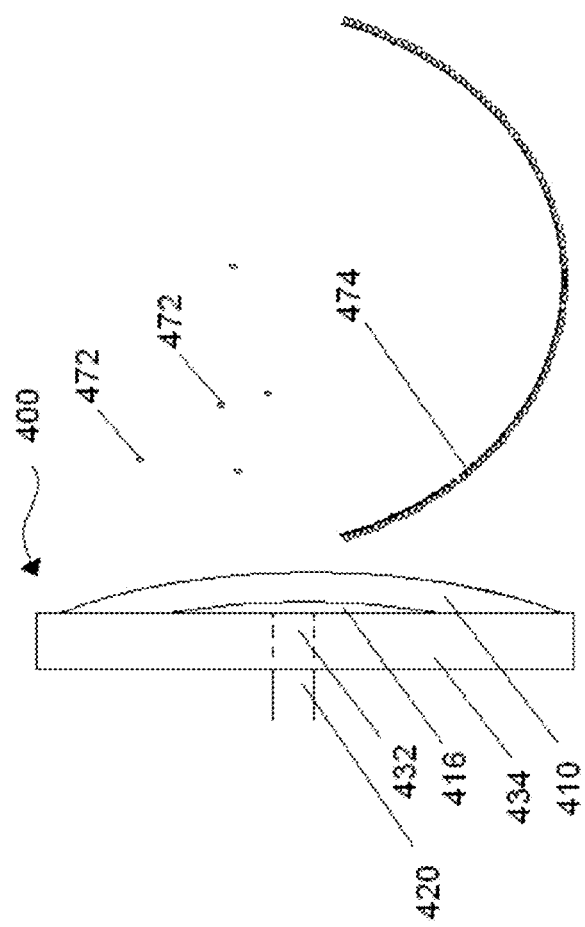
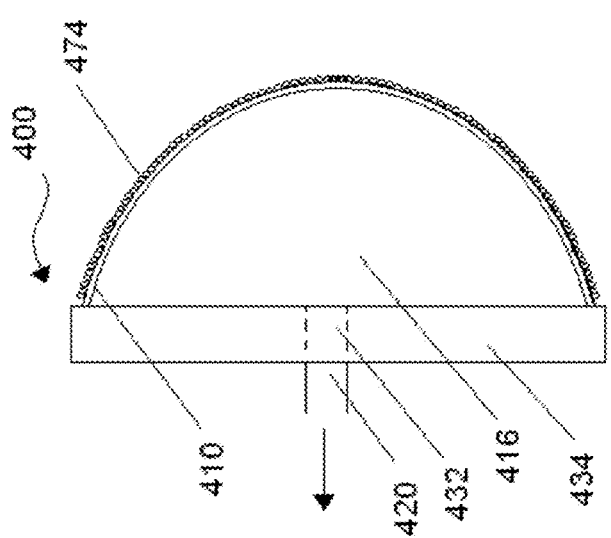

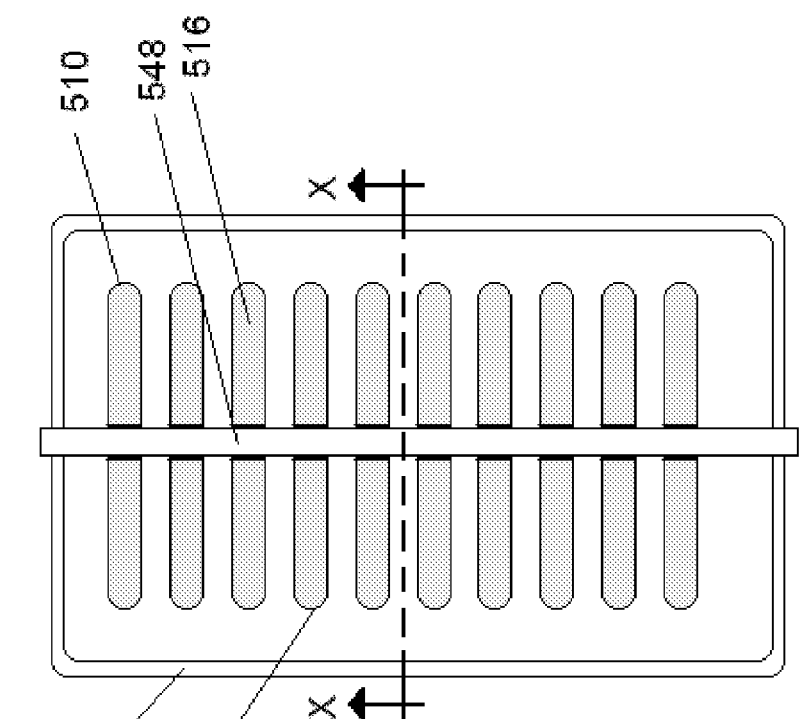
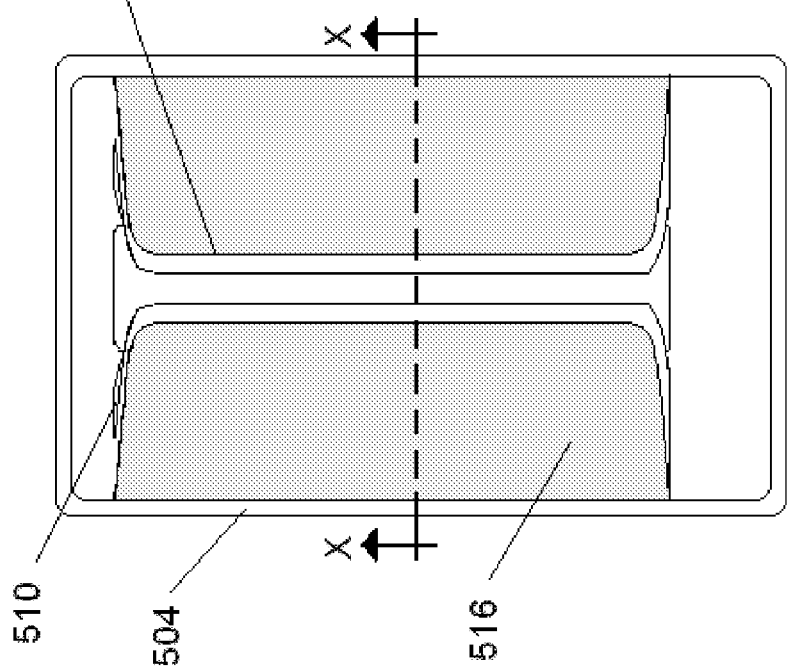
Fig. 5d
Fig. 5c

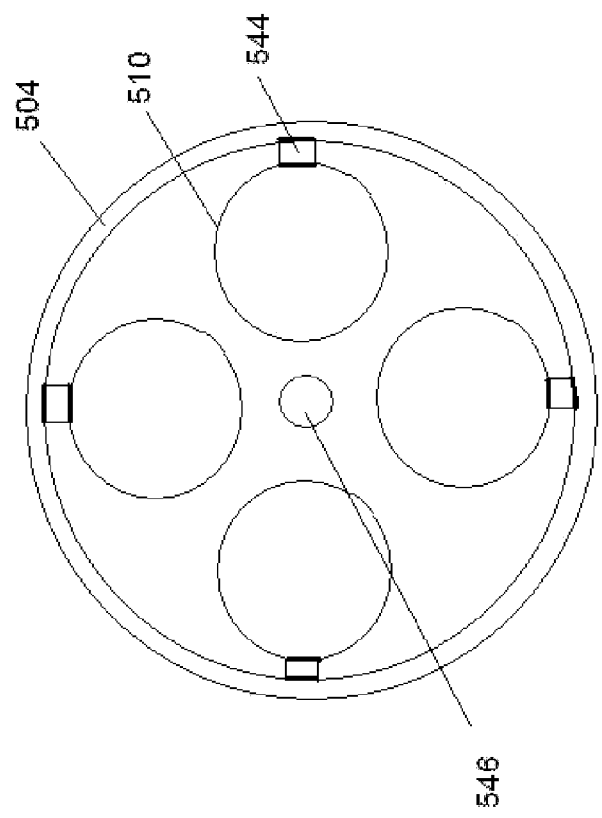
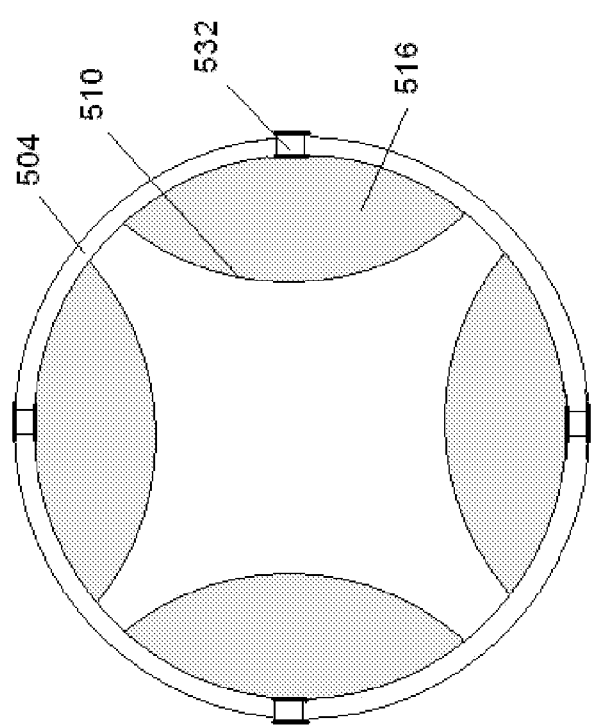
Fig. 6a
Fig. 6b

800

801
couple an elastic support to a surface within a cell culture vessel, the elastic support and the surface forming a chamber with an interior cavity

803
inflate the interior cavity

805
add cells to the cell culture vessel

807
incubate the cells within the cell culture vessel

809
sense one or more of pressure, temperature, oxygen concentration, and analyte concentration

811
alter the configuration of the elastic support to detach the cells from the elastic support, wherein altering the configuration includes at least one of inflating or deflating the elastic support

813
collect the detached cells

DYNAMICALLY ALTERABLE CELL SUPPORT

CROSS-REFERENCE TO RELATED APPLICATION

This application is a national phase entry under 35 U.S.C. §371 of International Application No. PCT/US2011/026346, filed on Feb. 25, 2011, which is incorporated herein by reference in its entirety.

BACKGROUND

Bioreactors are commonly used for large-scale cell culture. Non-adherent cells can be cultured in suspension. However, adherent cells are provided an attachment surface in order to maintain basic functions such as cell-cell signaling, growth, and proliferation. The topography of the attachment surface can influence morphology and function, and some adherent cells display a preference for textured surfaces. Extracellular matrix (ECM) components are produced and secreted by the cells to anchor the cells to the surface and to one another. As surface texture increases the total surface area available for ECM anchorage, adherent cells may adhere more firmly to textured attachment surfaces than to smooth surfaces.

Typically, a small number of adherent cells are added to a liquid growth medium and placed in a vessel with the attachment surface. The cells adhere to the attachment surface and proliferate, gradually spreading in a monolayer or multi-layer structure across the available surface. If the cells are not removed, contact inhibition disrupts the cell growth cycle. Therefore, in order to obtain viable cells, the cells are generally removed from the attachment surface through immersion in a removal solution. Removal solutions typically include one or more proteolytic enzymes, such as trypsin, and/or a metal ion chelator, such as EDTA. The removal solution cleaves ECM components and sequesters calcium ions, disrupting the cell-cell and cell-surface bonds. The adherent cells are released from the surface and from neighboring cells, and are then washed and collected by various recovery techniques.

BRIEF DESCRIPTION OF THE FIGURES

The presently disclosed subject matter is particularly pointed out and distinctly claimed in the concluding portion of the Specification. The foregoing and other features of the present disclosure will become more fully apparent from the following Detailed Description and appended Claims, taken in conjunction with the accompanying Figures. Understanding that these Figures depict example embodiments in accordance with the disclosure and are, therefore, not to be considered limiting of its scope, the disclosure will be described with additional specificity and detail through use of the accompanying Figures, in which:

FIGS. 4a-4d illustrate side views of an illustrative embodiment of an elastic support in operation;

FIGS. 5a-5d illustrate sectional views of an illustrative embodiment of a cell culture vessel comprising elastic supports;

FIGS. 6a-6d illustrate sectional views of the cell culture vessels of FIGS. 5a-5d taken along lines X-X;

FIG. 8 shows a flow chart of a method for culturing adherent cells on an elastic support;

DETAILED DESCRIPTION

Figure 1:
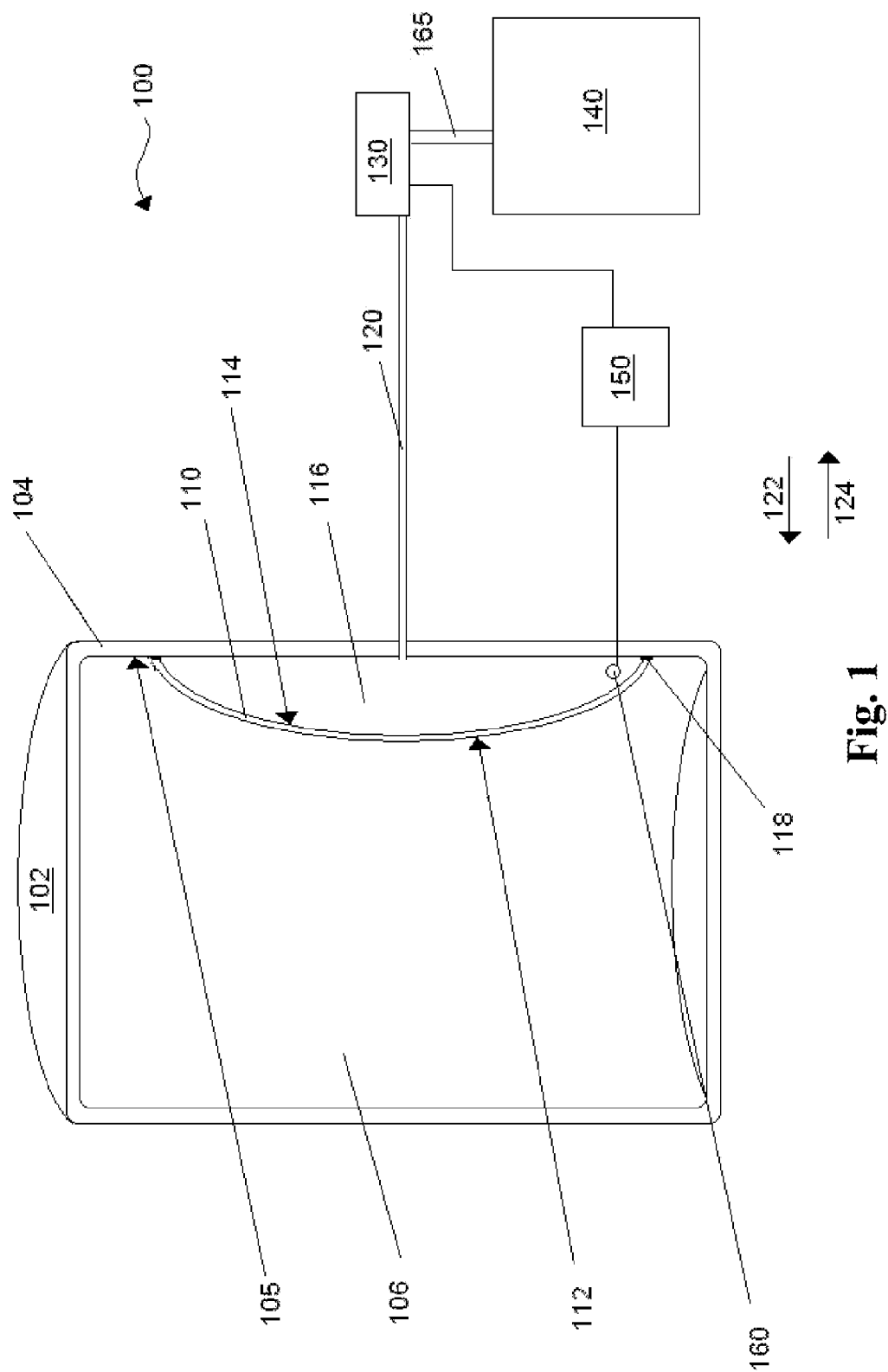
FIG. 1 illustrates a block diagram of an illustrative embodiment of a cell culture system with a dynamically alterable cell support.

The present Description sets forth various examples along with specific details to provide a thorough understanding of claimed subject matter. It will be understood by those skilled in the art, however, the claimed subject matter may be practiced without some or more of the specific details disclosed herein. Further, in some circumstances, well-known methods, procedures, systems, components and/or circuits have not been described in detail in order to avoid unnecessarily obscuring claimed subject matter. In the following Detailed Description, reference is made to the accompanying Figures, which form a part hereof. In the Figures, similar symbols typically identify similar components, unless context dictates otherwise. The illustrative embodiments described in the present Detailed Description, Figures, and Claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and make part of this disclosure.

The present disclosure is drawn, inter alia, to methods, systems, and articles for use with a dynamically alterable cell support. The use of removal solutions to detach adherent cells from a support surface can cause cell membrane damage, alteration, and/or undesirable triggering of morphogenic changes. Additionally, existing protocols for the harvesting of cells from support surfaces such as bioreactor disks require high temperature, centrifugation, wash/rinse steps, and/or other cell stressors. For example, removal solutions may change osmotic pressure and/or intracellular pH. This may be disadvantageous if the cells are to be used, for example, in complex tissue engineering applications. As another example, removal solutions may cleave membrane surface proteins, hampering efforts to study cell membrane surface molecule interactions. As still another example, increased pressure against the cell membrane caused by repeated centrifugation to wash the removal solution from the cells may induce damage and/or undesired intracellular signaling events.

Extracellular matrix (ECM) components secreted by adherent cells imparts mechanical strength to the cell layer. The elasticity of the ECM as measured by atomic force microscopy may vary as much as 300-fold among cell types, ranging from 0.1 kiloPascal (kPa) for soft brain tissue to 430 kPa for calcifying bone (see Reilly, G. C., Engler, A. J., "Intrinsic extracellular matrix properties regulate stem cell differentiation." Journal of Biomechanics (2009), doi: 10.1016/j.jbiomech.2009.09.009). Endothelial cells of the vasculature, muscle cells (e.g., myocardial cells), and bone cells (e.g., osteoblasts) are some non-limiting examples of cell types that form relatively inelastic ECM and correspondingly less flexible cell layers. These and other cell types typically require different mechanical environments for proper growth.

As described in further detail below, a dynamically alterable support is an elastic cell support that may be altered at a large scale (e.g., expanded and/or contracted) to induce mechanical removal of an adherent cell layer from a surface of the support. The expansion and/or contraction of the elastic support may exceed the flexibility of the adherent cell layer. Thus, the adherent cell layer or some portion thereof may be mechanically detached from the elastic support without the use of damaging removal solutions to harvest the cells, allowing the preservation of surface molecules, cell-cell ECM connections, and/or cellular morphology. Additionally, the use of an elastic support as described herein may allow metrics such as stiffness/compliance, shape, and curvature to be altered according to cell type. A dynamically alterable support may be provided for use with any cell culture vessel or bioreactor.

The present disclosure describes a dynamic adherent cell support. Some example dynamic cell supports may include an expandable elastic support layer with a first surface and a second surface. The first surface includes one or more textured surface portions. The expandable elastic support layer is configured to assume a first configuration in response to a first applied tension or pressure and to assume a second configuration in response to a second applied tension or pressure. A fastener is continuously coupled to the expandable elastic support layer. The elastic support layer includes an integrated inelastic material. The first surface includes one or more non-textured surface portions adjacent to one or more textured surface portions. Some textured surface portions may have a hydrophobic coating and/or a hydrophilic coating. The elastic support layer is configured to include a relaxed three-dimensional configuration and an expanded three-dimensional configuration and is selected to be permeable to a component of a cell culture medium in the expanded three-dimensional configuration. The elastic support layer can include a plurality of pores. In some examples, the pores expand in response to fluid pressure.

The present disclosure also describes a cell culture system for adherent cells. Some example systems may include a cell culture vessel, an elastic support, and/or a coupler. The elastic support has a first surface and a second opposite surface. The first surface has one or more textured surface portions and the second surface is coupled to an interior surface of the cell culture vessel. The elastic support and the interior surface of the cell culture vessel form a sealed chamber within the cell culture vessel. The sealed chamber has an interior at least partly defined by the second surface of the elastic support and the interior surface of the cell culture vessel. The coupler is disposed through the elastic support and/or the interior surface of the cell culture vessel, and forms a passage in fluid communication with the interior of the sealed chamber. The elastic support is configured to assume a first configuration in response to a first applied tension or pressure and to assume a second configuration in response to a second applied tension or pressure. In some examples, textured surface portions of the elastic support include an integrated inelastic material and/or a non-textured surface portion adjacent to a textured surface portion. Some example systems include a fluid transport system coupled to the coupler and in fluid communication with the sealed chamber. The fluid transport system includes a fluid displacement device, such as a pump and/or a hydraulic cylinder. Some example systems include a controller coupled to the fluid transport system. The controller is configured to control fluid pressure within the sealed chamber. Some example systems include a sensor operatively coupled to the sealed chamber.

The present disclosure also describes a method for culturing cells. Some example methods may include allowing cells to at least partially adhere to a surface of an elastic support in a cell culture vessel, and altering the configuration of the elastic support to detach the cells from the elastic support. Altering the configuration of the elastic support may include inflating and/or deflating the elastic support. The elastic support is inflated and/or deflated with a fluid. Some example methods also include sensing a resonant frequency of the elastic support and/or a fluid pressure of the fluid with a sensor. The sensor and the elastic support are operatively coupled to a controller. Alteration of the configuration of the elastic support is controlled by the controller based on the resonant frequency and/or fluid pressure sensed by the sensor. In some examples, the fluid is a liquid growth medium.

The present disclosure also describes a method for manufacturing a cell culture apparatus. Some example methods may include providing an elastic support layer and a hollow chamber that has an interior surface with a fluid portal, and coupling the elastic support layer to the interior surface. The elastic support layer and the interior surface enclose a void in communication with the fluid portal. The elastic support layer is configured to assume an inflated configuration in response to applied tension or pressure and to assume a relaxed configuration in response to release of the applied tension or pressure. Some example methods may also include coupling a fluid conduit to the fluid portal and/or coupling a pressurizing device to the fluid conduit.

As used herein, a "cell culture vessel" can be any vessel in which an organism (e.g., one or more cells) is grown and/or cultured. Examples of cell culture vessels include but are not limited to petri dishes, multi-well plates, microtiter plates, roller bottles, and screwcap flasks. The term "cell culture vessel" is intended to encompass bioreactors. A "bioreactor" can be any device or system used to provide an environment for supporting the growth or production of an organism or a substance produced by an organism. For example, a "bioreactor" can include a vessel for growing cells/tissues continuously and/or in batches. A bioreactor and/or cell culture vessel can include one or more "walls" surrounding an interior void. As used herein, the term "wall" may refer to any portion of the structure surrounding the interior void or within the void, including but not limited to a side, a top, and/or a bottom of the bioreactor/vessel. A bioreactor may also include one or more automated systems such as a temperature control system, a pressure control system, a fluid circulation system, etc. A bioreactor can include a sensor, a temperature control device, a liquid addition/removal device, a gas addition/removal device, a mixing/agitating device, a cell growth surface, a centrifugation device, a cell counting/sorting device, a radiant energy source, a controller, and/or other devices.

As used herein, an "elastic material" can be any biocompatible and/or non-biodegradable material that deforms under stress (e.g., stretches or changes conformation in response to applied pressure and/or tension) and at least partially or completely returns to its original shape/conformation upon removal of the stress. An elastic material can include but is not limited to an elastomer (e.g., acrylic elastomers, polyurethane elastomers), a polymer, a copolymer, a terpolymer, silicones (e.g., NuSil Technologies CF19-2186, Dow Corning HS3), acrylic/polyurethane elastomers (e.g., 3M VHB 3910 acrylic), and/or any natural, synthetic, or semi-synthetic material, alone or in any combination. A "polymer" as used herein can be any naturally occurring or synthetic material composed of linked monomers. A polymer may include one or more of a "copolymer" and/or a "terpolymer." A "copolymer" can be any polymer including at least two different monomeric species A and B (e.g., ether and propylene), which can be arranged in any way (e.g., alternating A and B monomers, alternating A and B polymers, repeated sequences, randomly disposed, block arrangements, etc.). A "terpolymer" can be any polymer including at least three different monomeric species, or any molecule including four or more different monomer species in any arrangement. "Polymer" as used herein can encompass polymers with any and all secondary, tertiary, and/or quaternary structures, side groups. An "elastomer" as used herein can be any amorphous polymer. A "silicone" as used herein can be any polymer that includes silicon.

As used herein, a "support" or "support layer" can be any item to which an adherent cell can attach in a cell culture. As used herein, an "elastic support" or "elastic support layer" or "dynamically alterable support" can be any cell support/support layer that includes an elastic material and/or exhibits one or more elastic properties. An elastic support can include an "elastic material" (e.g., nylon). Additionally, an elastic support can include one or more integrated or adhered inelastic or relatively inelastic elements (e.g., particles of calcium carbonate, calcium phosphate, ceramic, glass, plastic, polymer, etc.). An elastic support may be dynamically altered on a large scale by inflating, stretching, expanding, and/or by releasing tension on an inflated/stretched/expanded elastic support. The dynamic alteration may change the three-dimensional shape of the elastic support to cause the release of a cell layer from the elastic support. This alteration may be done rapidly and/or forcefully to aid the release of cells. In some examples an elastic support may be a single layer of an elastic material. In other examples, an elastic support may have two, three, or more than three layers of elastic material (e.g., a laminate of two or more materials).

An elastic support may have any suitable three-dimensional structure (e.g., flat sheet, film, disc/plate, cylinder, scaffold, sphere, etc.), which may change as tension is applied to the elastic support. An elastic support may have an initial "relaxed" configuration (e.g., a first configuration) while under minimal or no stress and may have a second, "inflated" configuration while under stress. In the relaxed configuration, the elastic support may appear deflated, wrinkled, and/or slack. Tension may be applied to the inner surface, outer surface, and/or to one or more edges of the elastic support (e.g., by pulling, pushing, stretching, and/or filling with a fluid such as a gas or liquid), herein referred to as "inflation." Inflation of the elastic support may stretch, expand, pull, and/or otherwise deform the elastic support into an "inflated" (e.g., expanded) configuration in which the thickness of the elastic support is decreased and the surface area is increased relative to the relaxed configuration. In some examples, an elastic support may be inflated by a fluid (e.g., a liquid or a gas) to reach an expanded balloon-shaped inflated configuration that provides a spherical interior or exterior surface for cell growth. Therefore, an increase in surface area of the elastic support may occur upon inflation. Alternatively, there may be little or no change in the surface area of the elastic support upon inflation. For example, an elastic support may have an inflated configuration as a result of a change in shape (e.g., a change from a concave shape to a convex shape), which may be induced by fluid pressure or mechanical force.

Inflation may cause a change in the shape, surface texture, surface area, and/or thickness of the elastic support. For example, an elastic support that includes materials with zones of differing elasticity may have a rippled appearance when partially inflated, and may appear smooth when the elastic support is fully inflated. In another example, an elastic support may be inflated within a cell culture vessel to support cell growth within the inflated portion. The inflation of the elastic support may cause its outer surface to press against a textured interior surface (e.g., a wall) of the cell culture vessel, thus presenting the texture of that surface. When the elastic support is at least partially deflated and is no longer pressing against the textured surface, the elastic support may appear smooth and tube-shaped. In yet another example, the elastic support may have a concave three-dimensional shape in the relaxed configuration and a convex three-dimensional shape in the inflated configuration, or vice versa. The elastic support may be 'flipped' suddenly from one configuration to the other by mechanical or fluid pressure, such as by forcing air, a gas, or a mechanical element such as a piston against a surface of the cell support (e.g., against the surface opposite the cell growth surface). Such a dramatic change of shape may maximize mechanical detachment forces while staying within a desired strain range for the elastic material.

In some examples, one or more changes induced by inflation of the elastic support may be measured and/or detected mechanically. For example, strain gauges coupled to or embedded within the elastic support may be used to measure strain/tension. Displacement sensors, mechanical contact sensors, and other devices may be used to detect changes in size. Some or all of these changes may be visually observable and/or measured by an optical detector (e.g., enlarging/shrinking, change in curvature, visible thinning evidenced by decreased opacity of the elastic support material, etc.).

Release or reduction of the applied stress, herein referred to as "deflation," may cause the elastic support to resume a relaxed configuration. A relaxed configuration after deflation may be different from the initial relaxed configuration. For example, the elastic support may contract upon release of tension, but may not completely resume the initial relaxed configuration due to incomplete contraction. In other words, the dimensions of the relaxed configuration may be greater than the dimensions of the initial configuration but less than those of the inflated configuration.

The degree of contraction required may be low (e.g., less than 10% or less than 30%), moderate (e.g., approximately 20-50% or 30-80%), or high (70-90%, 80-95%, 90-99%, or 95-100%). As an example, a low or moderate degree of contraction may be required for an elastic support that is suddenly 'flipped' from a convex configuration to a concave configuration (or vice versa) as described above. In contrast, a moderate or high degree of contraction may be required where a sudden and/or forceful contraction of an inflated elastic support is needed to detach an adhered cell layer in a single inflation/deflation event.

Repeated minor strains can cause significant detachment of an adherent cell layer. Therefore, a low or moderate degree of contraction may be sufficient where multiple inflation/deflation cycles are used to cyclically weaken the attachments of adherent cells to the elastic support. During an inflation/deflation cycle, an inflated elastic support may be inflated, deflated, and then re-inflated (or vice versa). The inflation/deflation events within a cycle may occur rapidly, with the configuration of the elastic support maintained at a steady state for some period of time between events. Alternatively, inflation/deflation events within a cycle may occur more slowly, with the configuration of the elastic support fluctuating continuously throughout the cycle. Inflation/deflation cycles may occur at rates within the ranges of 1-15 minutes per cycle, 10-30 minutes per cycle, 30 minutes to 1 hour per cycle, 1-10 hours per cycle, 6-12 hours per cycle, or 12-48 hours per cycle. Alternatively, inflation/deflation cycles may be rapid, such as at a rate of 1-1000 cycles per second or 1-1000 cycles per minute. In some examples, liquid cellular medium may be replaced with air before or during the cycling process in order to facilitate faster oscillation. The liquid cellular medium may or may not be replaced after the cycling process is completed. Therefore, cell detachment may involve varying the pressure slightly over many cycles with relatively minor contraction of the elastic support. The effect of such deflations may be very small (e.g., in the micro- or millistrain range) and may be detected with a strain gauge/sensor.

An elastic support may be used to support cell growth in the relaxed conformation, in an inflated conformation, and/or in a partially inflated conformation. For example, an elastic support may be shipped and stored in the relaxed conformation (e.g., folded, rolled, flat, etc.), and subsequently expanded to an inflated conformation in order to pre-strain elastic materials within the elastic support, thereby increasing its elastic range. The elastic support may then be partially deflated to a desired intermediate size, which may be determined based on factors such as the mechanical requirements the cell type(s) to be grown on the elastic support, the force required to detach the cells from the elastic support, the number of inflation/deflation cycles to be used, and/or the physical diameters of the interior of the cell culture vessel.

Cells may be grown on the exterior surface or the interior surface of an inflated support. To grow cells on the interior of an inflated elastic support at atmospheric pressure within a cell culture vessel, the pressure within the cell culture vessel (e.g., exterior to the inflated elastic support) may be reduced to at least partial vacuum (below atmospheric pressure). When the cells have grown on the interior surface of the inflated elastic support, the elastic support may be made to expand further or to contract by increasing or decreasing the pressure difference between the inside and the outside. This may be done by adjusting the pressure within the expandable support, adjusting the pressure within the cell culture vessel, or both. The expansion/contraction of the expandable support may exert a mechanical strain on portions of the cells adhered to the interior surface of the elastic support, helping to detach the cell layer.

Alternatively, cells may be grown on the exterior surface of an inflated elastic support. In either case, the pressure within an inflated elastic support (e.g., within the balloon) may be greater than or approximately equal to the surrounding pressure. In some examples, either or both pressures may be a convenient working pressure, such as atmospheric pressure.

An elastic support may have a first surface for cell adhesion and a second, opposite surface, either or both of which may be nonporous, porous, textured, smooth, selectively permeable, etc. The permeability of an elastic support to liquids, gasses, and/or molecules of various sizes may increase as the elastic support is inflated. For example, an elastic support may include pores that widen as cell culture medium is directed against the inner surface to inflate the elastic support, allowing one or more components of the cell culture medium to diffuse across the elastic support. In this example, the elastic support may be inflated with a liquid medium that includes one or more nutrients for cell growth in order to continuously supply nutrients to the cells. The pores may widen/enlarge due to mechanical strain as the surface is stretched, and may reach diameters within the ranges of 0.01-0.1 µm, 0.1-0.2 µm, 0.1-1.0 µm, 1-5 µm, 1-20 µm, 10-100 µm, and/or 50-1000 µm. Alternatively, the folding and unfolding of polymer chains as the elastic support is inflated may result in small gaps between some of the chains, cause the elastic support to become permeable to gases and/or small molecules such as water and glucose.

A permeable elastic support may allow different gas or liquid flows to be supplied to cells as they grow and/or pass from one life cycle stage to another. Alternatively, further inflation of a porous or permeable elastic support may aid release of cells from the outer surface by allowing gas or liquid to flow outward from within the inflated elastic support, which applies force against the underside of the cell layer, while also stretching the connections between the cells and the outer surface.

As used herein, a "textured surface" can be any surface with one or more three-dimensional (e.g., raised or depressed) surface features. Similarly, a "textured surface portion" can be a textured surface extending across some portion of the surface. As an example, substantially all of the outer surface of an elastic support may be a textured surface designed to encourage or enhance cell adhesion. Alternatively, an elastic support may have an outer surface that includes one or more textured surface portions surrounded by non-textured or less-textured (e.g., relatively smooth) surface portions. A textured surface or textured surface portion on an elastic support may be created or altered as a result of inflation/deflation of the elastic support and/or with a hydrophobic/hydrophilic surface coating as described in further detail below.

An elastic support may include a mixture of materials with varying degrees of elasticity, such that inflation of the elastic support causes some portions of the surface to protrude more than other portions. A textured surface may have features including but not limited to ridges, grooves, spheres, pores/channels, and/or protrusions in any shape (e.g., conical protrusions, columnar protrusions, etc.). Such features of a textured surface may be characterized, for example, by a spatial pitch in the range of 60 µm to 10 mm, 6 µm to 60 µm, or 10 mm to 100 mm, and/or other aspects such as radius of curvature and/or sharpness. One or more features of a textured surface may protrude in response to inflation to form a surface texture. For example, an elastic support containing embedded inelastic polymer beads may be inflated, causing the thickness of elastic portions to decrease while the thickness of the embedded hard spheres remains unchanged. The pitch may be determined by the original packing density of the spheres within the elastic support and by the degree to which the elastic support stretches during inflation. The radius of curvature may be determined by the protruding texture elements. Shapes other than spheres, such as cones, rods, cubes, dodecahedrons, or other polyhedrons may be contained within the elastic to provide a texture suitable for a particular cell type. For example, features with sharper edges may be embedded in an elastic support used for growing cells such as osteoblasts, which prefer to grow on textured surfaces with sharp edges.

In another example, a surface of an elastic support may be rippled, pleated, folded, and/or ruffled prior to inflation of the elastic support. Portions of the unexposed surface may have textures that are exposed upon inflation of the elastic support as described above. In yet another example, pores/pitting on the surface of a deflated elastic support may be stretched or altered upon inflation of the elastic support, resulting in a textured surface. Alternatively, inflation of an elastic support may reduce or eliminate three-dimensional surface texture.

For example, if cells are to be grown on the inside of the elastic support, the elastic support may be inflated against a textured surface as described above. A textured surface may also be provided on or in an elastic support by pressing a textured template surface (e.g., a textured plate or roller) against a relatively flat or sheet-like elastic support that is held within a ring or a frame, thus stretching and texturing the elastic support in the same step. Such textured template surfaces may be interchangeable, and may be designed to change the surface texture of the elastic support before and/or during use. This could be controlled, for example, by using servomotors to move a textured roller behind an elastic support that is stretched within a frame in a cell culture vessel.

FIG. 1 illustrates a block diagram of an illustrative embodiment of a cell culture system with a dynamically alterable cell support. This Figure shows an elastic support surface along an inner wall of a cell culture apparatus. As illustrated, cell culture system 100 may include cell culture vessel 102 with one or more walls 104 at least partially enclosing vessel interior 106. Walls 104 may be side, top, and/or bottom walls. Fluid conduit 120 may be coupled to cell culture vessel 102. Fluid displacement device 130 may be coupled to fluid conduit 120, fluid source 140, second conduit 165, and/or controller 150. Controller 150 may be coupled to one or more sensors 160.

Elastic support 110 may be coupled to interior surface 105 of cell culture vessel 102 by one or more fasteners 118 to form sealed chamber 116. In some examples, elastic support 110 and/or a component coupled to elastic support 110 (e.g., a frame) may be sealed against interior surface 105 with a compression gasket. In other examples, elastic support 110 may be a hollow component (e.g., a balloon or bag shape) with an aperture, and may be mechanically clamped or sealed around the aperture to fluid conduit 120 and/or to interior surface 105. In still other examples, a portion of elastic support 110 may be inserted through an aperture in wall 104 and/or interior surface 105, and a remaining portion of elastic support 110 may be sealed against an exterior portion of cell culture vessel 102 and/or another component of system 100, such as fluid conduit 120.

Elastic support 110 may include first surface 112 and second surface 114. Second surface 114 may be exposed along the interior of sealed chamber 116 and first surface 112 may be exposed to vessel interior 106. The interior of sealed chamber 116 may be coupled to fluid source 140 via fluid conduit 120.

Fastener 118 can include a hardware device such as a threaded post, clamp, or flange. Alternatively, fastener 118 can include an adhesive, a gasket, a suction device, and/or any other coupling feature configured to couple elastic support 110 to a surface, such as an interior or exterior surface of wall(s) 104. In some examples, fastener 118 and/or elastic support 110 may be permanently coupled to an interior surface of a cell culture vessel by welding, melting, an adhesive, or by any suitable means known in the art. In other examples, fastener 118 may be removably coupled to an interior or exterior surface of a cell culture vessel, a fluid conduit, a shaft/axis, or other structure.

Fastener 118 may include one or more components configured to mechanically stretch elastic support 110, such as one or more spring members, pistons, or any tensioning device known in the art. Alternatively, fastener 118 may be or include a compression gasket for sealing elastic support 110 against the side of one or more walls 104. In some examples, elastic support 110 may be bag-shaped or balloon-shaped, and fastener 118 may be a ring clamp that is used to seal the opening of elastic support 110 to another component, such as fluid conduit 120. In other examples, elastic support 110 may be inserted through an aperture in wall 104 and fastener 118 may be a gasket, hollow threaded post, or other device configured to hold the edges of elastic support 110 against an exterior surface of wall 104. Examples of attachment configurations are provided in FIGS. 5a-6d and in the accompanying description below. In some examples, such mechanical components may augment or replace the deforming function of the fluid system shown.

Cell culture vessel 102 may be any type of cell culture vessel as described above. For example, cell culture vessel 102 may be a cell culture chamber of substantially any commercially available bioreactor. Controller 150 may monitor one or more conditions within any one or more components of the cell culture system 100, such as temperature, fluid pressure, and/or time. Controller 150 may operate fluid displacement device 130 in response to a user command. Alternatively, controller 150 may operate fluid displacement device 130 automatically, for example, in response to data received from one or more sensors such as sensor 160. This may provide automatic inflation/deflation of elastic support 110.

Controller 150 may include a processor endowed with operating logic configured to send a command to fluid displacement device 130, such as a command to increase or decrease fluid pressure within sealed chamber 116. Such a command may be based on a current growth process stage and/or a detected value from sensor 160. For example, during a "growth" stage commands may be sent to maintain a constant pressure in sealed chamber 116. In a "cell detachment" stage, controller 150 may send a command to fluid displacement device 130 to induce pressure oscillations in sealed chamber 116 in order to detach the cells from first surface 112. Controller 150 may also monitor/adjust other parameters of cell culture system 100, such as liquid medium exchange, pH, and/or temperature within vessel interior 106.

Fluid displacement device 130 can include a pump, a pneumatic device, a hydraulic device, a motor, a piston/cylinder, a screwpump device (e.g., an Archimedes screw), and/or any device for providing a fluid under pressure. Fluid may be drawn from fluid source 140, which can be a fluid reservoir and/or conduit. Some embodiments may optionally lack fluid source 140. For example, fluid may be added to, and retained by, fluid displacement device 130 and fluid conduit 120.

Sensor 160 can include one or more pressure sensors (e.g., a force transducer, a pressure transducer), strain sensors, temperature sensors, timers, oxygen sensors, and/or analyte sensors (e.g., configured to sense a secreted cell product) used to monitor cell growth or growth conditions. Sensor 160 may be disposed, for example, on interior surface 105, within sealed chamber 116, on or embedded within elastic support 110, and/or within vessel interior 106.

In one example, a sensor 160 may be configured to determine whether cells growing on elastic support 110 are confluent or nearly confluent. In this example, sensor 160 may be a strain sensor disposed on the surface of elastic support 110 and coupled to controller 150. Sensor 160 may be used to detect the resonant frequency of elastic support 110 under input forces (e.g., fluid pressure). Sensor 160 may send feedback to controller 150 relating to the resonant frequency, and controller 150 may use the data to track the added mass of adhered cells, thereby tracking cell growth. Sensor 160 may also send feedback to controller 150 relating to the resonant frequency of elastic support 110 when the elastic support is inflated/deflated to detach the cells, allowing controller to track or confirm cell detachment. Therefore, elastic support 110 may be automatically inflated/deflated by the controller based at least in part on sensor data.

In another example, sensor 160 may include a pressure sensor coupled to elastic support 110, fluid displacement device 130, and/or fluid conduit 120 to detect fluid pressure. Sensor 160 may send feedback to controller 150 relating to fluid pressure, for example, and controller 150 may respond to the feedback by sending a command to fluid displacement device 130 to increase or decrease fluid pressure within sealed chamber 116. In another example, sensor 160 may send feedback to controller 150 relating to the concentration of an analyte that increases in proportion to the number of cells adhered to elastic support 110. Controller 150 may respond to the feedback by determining (based on the concentration of the analyte) that the cells are confluent and sending a command to fluid displacement device 130 to rapidly decrease fluid pressure within sealed chamber 116 in order to release the adhered cells. The illustrated arrangement is merely one example, and is not intended to be limiting. In another example, fluid displacement device 130, controller 150, fluid source 140, fluid conduit 120, and/or second conduit 165 may be combined within a single apparatus.

In operation, fluid displacement device 130 may push a fluid into the interior of sealed chamber 116 through fluid conduit 120 in the direction shown by arrow 122. The increasing fluid pressure within sealed chamber 116 may inflate (e.g., stretch or expand) elastic support 110 as described above. Fluid displacement device 130 may also remove a fluid from the interior of sealed chamber 116 through fluid conduit 120 in the direction shown by arrow 124. Fluid displacement device 130 may include a pump, such as a hydraulic or pneumatic pump. In some examples, the fluid may pressurized within a reservoir, and the pressure may be reduced by opening a valve to the ambient pressure. In yet other examples, fluid displacement device 130 and reservoir may be combined in the form of a syringe pump, with the pressurizing and depressurizing being performed by the linear motion of a plunger.

The release of tension/fluid pressure may deflate elastic support 110. This may be done suddenly in order to enhance the removal of cells from elastic support 110. The fluid may be a gas, a liquid, or any combination of one or more gasses and/or liquids. For example, the fluid may be a liquid cell culture medium. Alternatively, the fluid may be a gas that includes ambient air pressurized by a pump or nitrogen drawn from a pressurized nitrogen supply. The fluid may instead be a liquid that includes deionized, filtered, distilled, or purified water, with or without a sterilizing or antibacterial agent.

Elastic support may be inflated/stretched and deflated/contracted by one or more mechanical devices, with or without additional fluid pressure. For example, a solid feature may be pushed by a piston or other device against a surface of the elastic support to inflate the elastic support, and pulled away to deflate the elastic support. As another example, one or more edges of the elastic support may be pulled outwardly from the center to inflate/stretch, and released to deflate, elastic support 110 to effect a change in surface area without changing curvature. In one example, elastic support 110 may be mechanically inflated or expanded within a cell culture vessel by pulling the top, side, and/or bottom edges of elastic support 200 outwardly away from the center.

In the inflated configuration, elastic support 110 may divide at least some portion of the interior of cell culture vessel 102 into two compartments. A liquid medium and cells may be supplied to one or both compartments (e.g., by fluid displacement device 130). Elastic support 110 may include pores/channels (see e.g., FIG. 2 with pores 208 and channels 226) to allow nutrients, waste products, and/or other molecules to move from one compartment to the other through elastic support 110. Examples of such elastic supports are discussed in further detail below.

Figure 2:
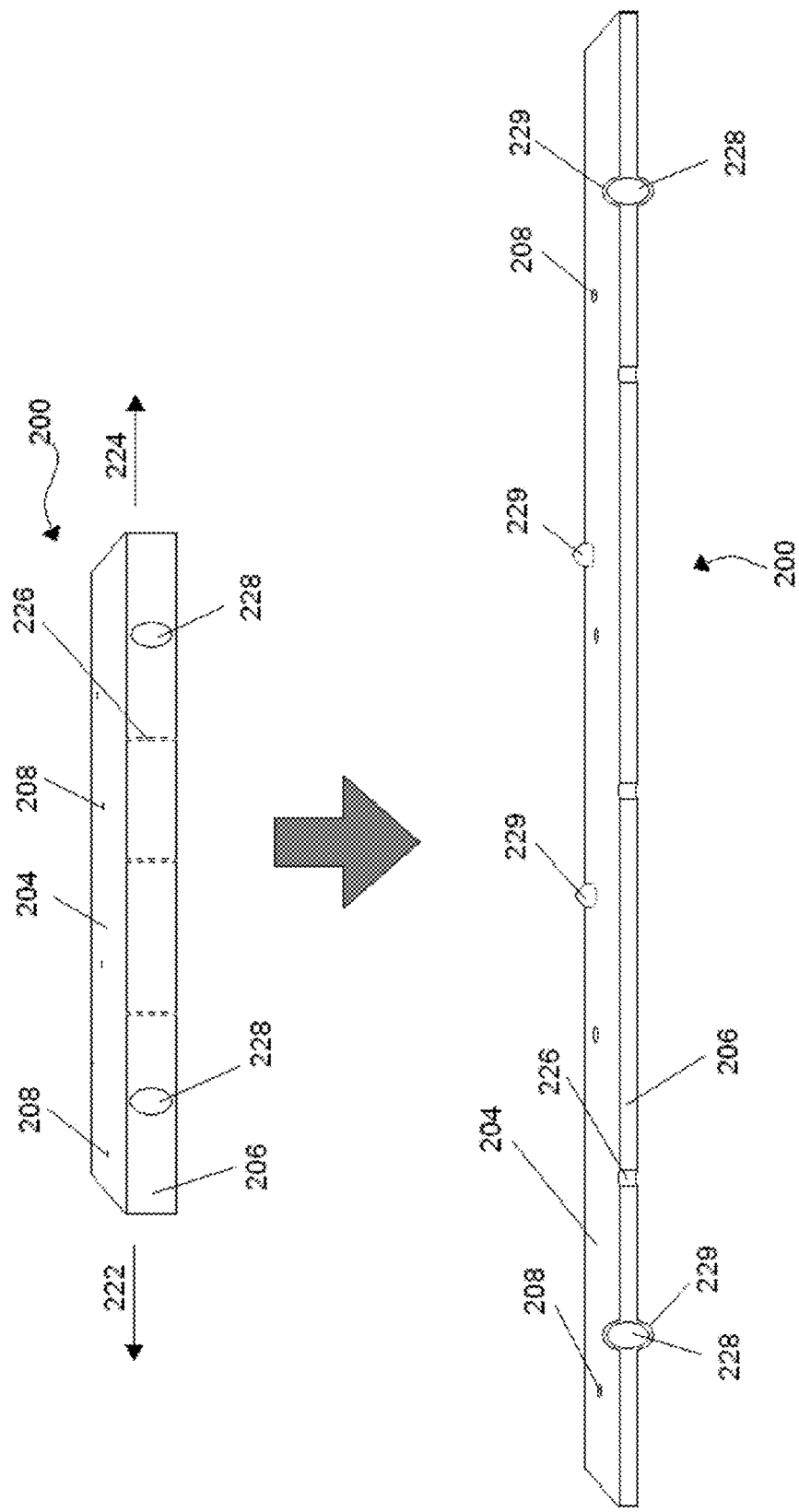
FIG. 2 illustrates perspective views of an illustrative embodiment of an elastic support with a relaxed configuration and an inflated configuration.

FIG. 2 illustrates perspective views of an illustrative embodiment of an elastic support with a relaxed configuration and an inflated configuration. Elastic support 200 is shown at the top of FIG. 2 in a relaxed three-dimensional configuration. Elastic support 200 may assume an inflated three-dimensional configuration, as shown at the bottom of FIG. 2, in response to tension applied by one or more mechanical devices (as depicted by arrows 222 and 224). Alternatively, elastic support 200 may assume an inflated three-dimensional configuration in response to fluid pressure (see FIGS. 4a and 4b). In the inflated three-dimensional configuration, elastic support 200 may have increased surface area and decreased thickness relative to the relaxed configuration, as indicated in FIG. 2. The change in thickness and surface area can typically be predicted via geometry and the material property known as Poisson's ratio, which varies by material. Elastic support 200 may be constructed with materials selected to achieve desired thickness and surface area changes during use. The changes in thickness resulting from inflation/deflation may be dynamically measured, for example, by placing electrodes on top and bottom surfaces of the elastic support and measuring capacitance changes as tension is applied.

Elastic support 200 may include pores 208 and/or channels 226 in one or both configurations. A channel 226 may be a conduit between two pores 208. Alternatively, channels 226 and pores 208 may be separate. In one example, pores 208 may be present on an outer surface 204 of elastic support 200 and may provide surface texture for cell adhesion without providing a passage through elastic support 200. Alternatively, pores 208 may pass provide passages through elastic support 200. Pores 208 and/or channels 226 may be altered in shape and/or diameter in response to inflation/deflation of elastic support 200. Alternately, pores 208 and/or channels 226 may be passages through relatively inelastic portions of elastic support 200 and may retain their sizes and shapes as the elastic support 200 deforms. For example, pores 208 and/or channels 226 may be hard plastic grommets. As another example, pores 208 and/or channels 226 may be passages through a less-elastic material embedded in elastic support 200 that changes in thickness/surface area at a different rate than the elastic support 200 upon inflation\deflation. Pores 208 and channels 226 may have a variety of shapes and may be distributed randomly or in predetermined patterns on or within elastic support 200.

As described above, elastic support 200 may include one or more integrated components/materials with varying degrees of elasticity, causing some portions of the surface to protrude more than other portions upon inflation/deflation. In FIG. 2, texture elements 228 are integrated inelastic components embedded within elastic support 200. In the deflated configuration (top), texture elements 228 may be minimally visible or not visible along outer surface 204, 206. In the inflated configuration, the decrease in thickness of elastic support 200 in surrounding areas may cause the protrusion of texture elements 228, forming textured surface portions 229. Texture elements 228 may be fully embedded within the thickness of elastic support 200 as shown, such that texture elements 228 remain covered by another material as they protrude. Alternatively, texture elements 228 may be partially embedded such that some portion of texture elements 228 is exposed in response to inflation of elastic support 200. Texture elements 228 may instead be more elastic than other portions of elastic support 200, becoming thinner than surrounding areas upon inflation and creating depressions/invaginations of outer surface 204, 206.

Pores 208 and/or channels 226 may be expandable in response to inflation of elastic support 200, allowing nutrients to be supplied to cells growing on elastic support 200. This expansion may cause elastic support 200 to be permeable to a component of a cell culture medium in the inflated three-dimensional configuration, but impermeable to the component in the relaxed three-dimensional configuration. The component may be, for example, glucose, another cell nutrient, or a component produced by the cells.

Figure 3A:
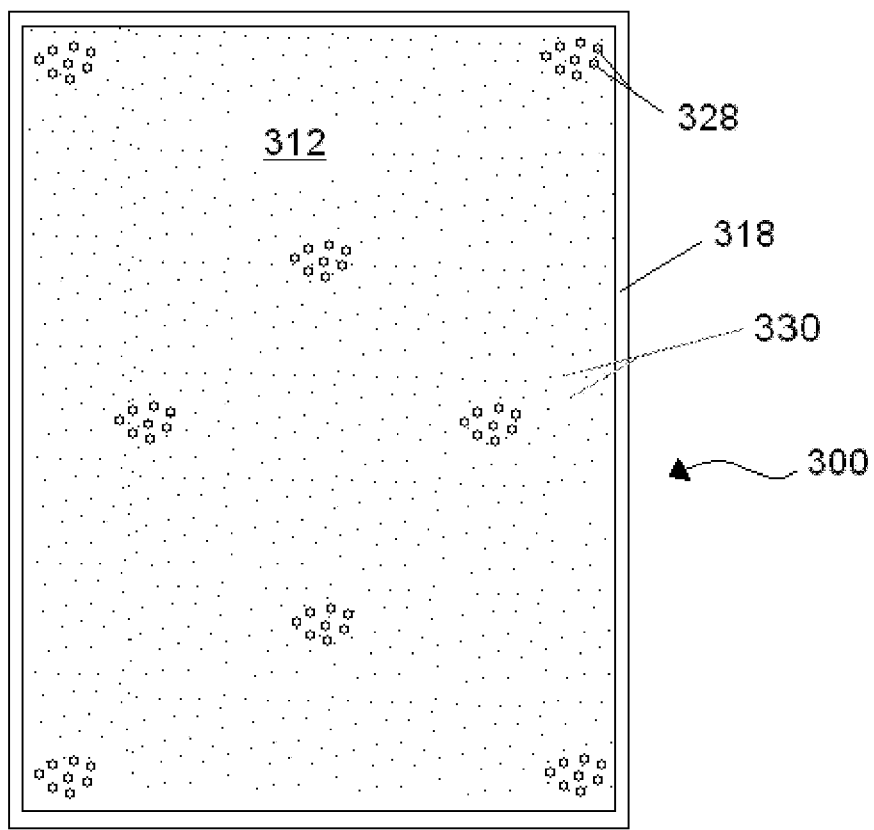
FIGS. 3a and 3b illustrate front and back views of an illustrative embodiment of an elastic support.
Figure 3B:
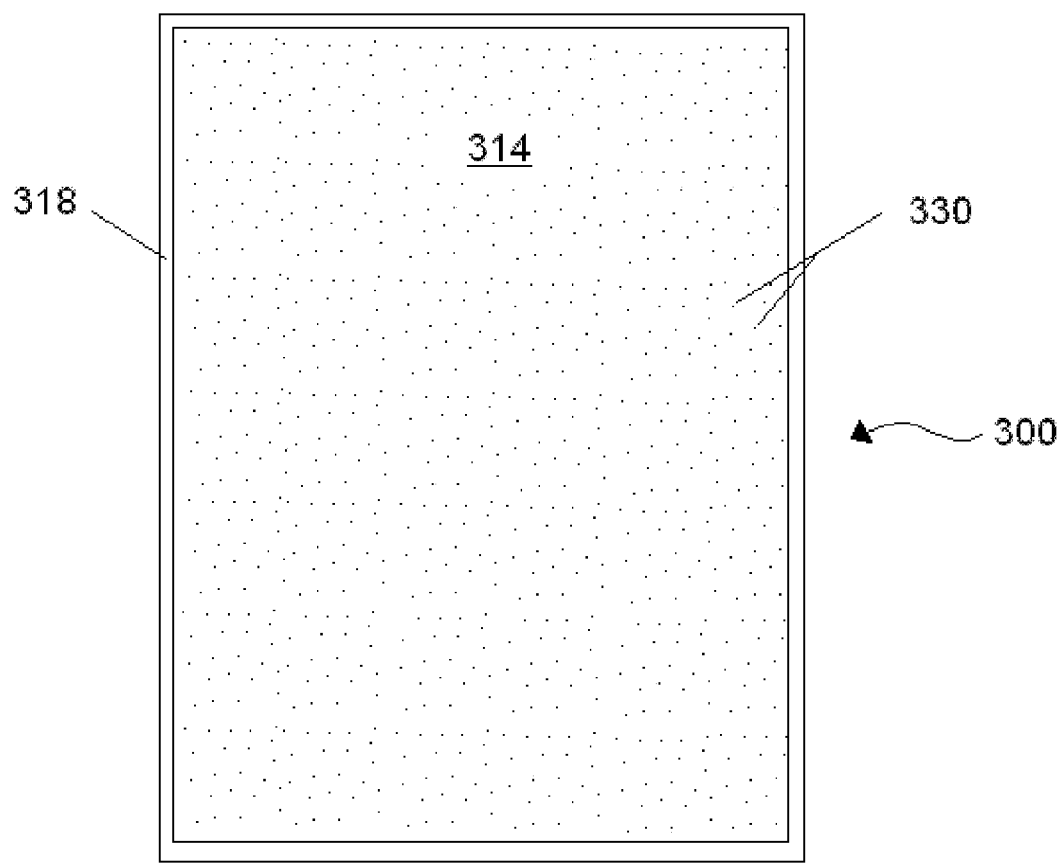

FIGS. 3a and 3b illustrate front and back views of another illustrative embodiment of an elastic support 300. First surface 312 of elastic support 300 (e.g., the "front" surface) may include, for example, one or more textured surface portions 328, channels/pores 330 (see also FIG. 2), and fastener 318. Second surface 314 of elastic support 300 (e.g., the "back" surface) may also include, for example, channels/pores 330 and fastener 318. In some examples, first surface 312 and/or second surface 314 may include a sensor such as sensor 160 (see e.g., FIG. 1).

Textured surface portions 328 can include one or more inelastic or less-elastic components, such as texture elements 228. Textured surface portions 328 may be arranged individually or in one or more groups along first surface 312. Some areas of first surface 312 (e.g., between textured surface portions 328) may be non-textured and/or less-textured, and may include one or more non-stick materials (e.g., a low-friction polymer such as polytetrafluoroethylene (PTFE)) integrated within elastic support 300 and/or coated onto the surface.

Elastic support 300 may have one or more surface coatings or textures that influence hydrophobicity or hydrophilicity. For example, first surface 312 may be designed with hydrophilic surface textures in some locations to enhance cell adhesion and hydrophobic surface texture in other areas to discourage strong adhesion to elastic support 300. A hydrophobic or hydrophilic surface texture may be, for example, a self-assembled monolayer (SAM) of molecules bound to an outer surface of elastic support 300. SAMs may be formed using methods known in the art. For example, an elastic support with an embedded and partially surface-exposed texture element with a gold or $Si/SiO_2$ outer surface portion may be incubated in 1 mM octadecanethiol in ethanol (for gold) or 1 mM octadecanetricholorosilane in toluene (for $Si/SiO_2$) for approximately 18 hours to create a hydrophobic SAM on the exposed gold or $Si/SiO_2$. To convert the surface texture from hydrophobic to hydrophilic, a protein solution (e.g., 1 mg/ml avidin in phosphate-buffered saline) may be applied to the elastic support, causing the protein to bind to the hydrophobic surface and rendering that surface hydrophilic. These methods and techniques are described by Deval J. et al., "Reconfigurable hydrophobic/hydrophilic surfaces in microelectromechanical systems (MEMS)" *J. Micromech. Microeng.* 14, pp. 91-95 (2004). Thus, elastic support 300 may be provided with specific locations encouraging cell adhesion and other locations discouraging cell adhesion.

A variety of surface textures and/or surface coatings may be provided on elastic support 300 to induce preplanned anchoring and growth of two or more cell types across first surface 312. In some examples, textured surface portions 328 may provide an initial attachment site for adherent cells, which may then proliferate across the non-textured portions of the surface. This may enhance the mechanical removal of the adherent cells upon deflation of elastic support 300. While textured surface portions 328 are shown in intermittent groupings across first surface 312, other arrangements are also possible. In one example, textured surface portions 328 may be arranged circumferentially around the outer periphery of elastic support 300. In another example, textured surface portions 328 may be arranged in the center of elastic support 300. In still another example, textured surface portions 328 may be dispersed along substantially all of first surface 312.

Fastener 318 can include any combination of components as described above with regard to fastener 118. In some embodiments, fastener 318 and/or elastic support 300 may be permanently affixed to an interior surface of a cell culture vessel, such as an interior wall of a bioreactor, by welding, melting, an adhesive, or by any suitable means known in the art. In other embodiments, fastener 318 may be removably coupled to an interior surface of a cell culture vessel, a fluid conduit, a shaft/axis, or other structure. Examples of attachment configurations are provided in FIGS. 5a-6d and in the accompanying description below.

Figure 5B:
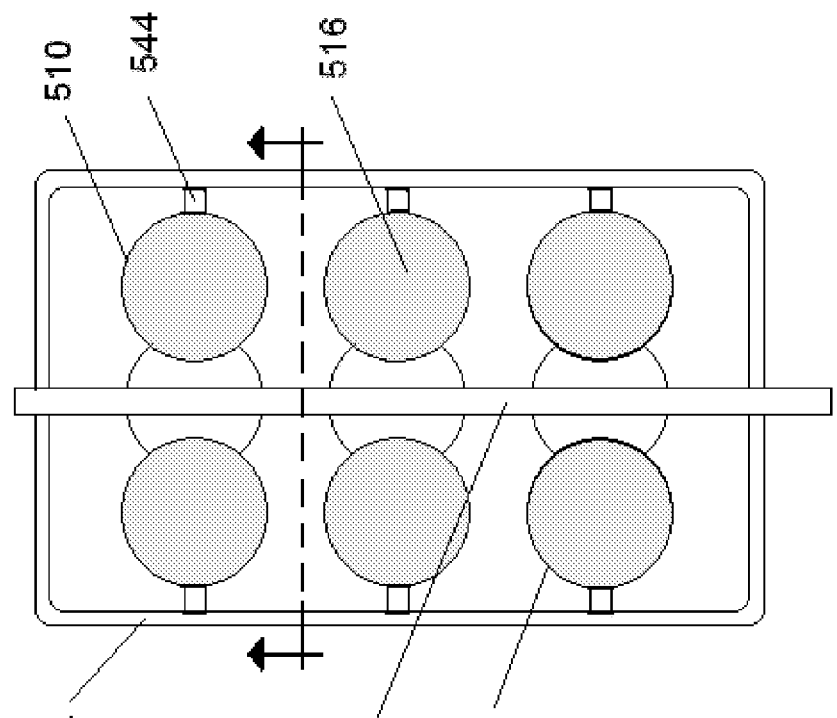
Figure 5A:
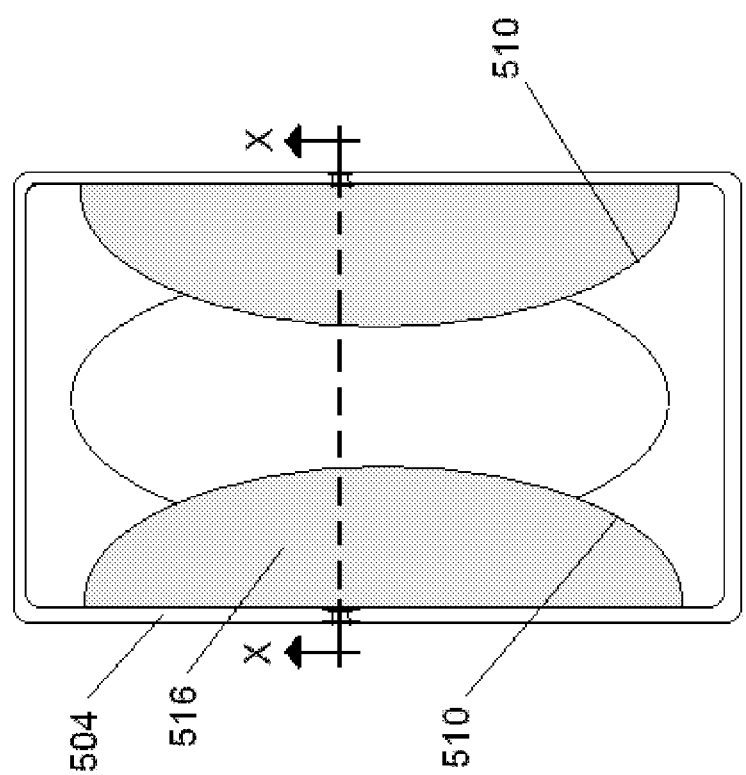

FIGS. 4a-4d illustrate side views of an illustrative embodiment of a support assembly having an elastic support for illustrating an operation of the elastic support. FIG. 4a shows a support assembly 400 including an elastic support 410 coupled to support base 434 to form a sealed chamber with an interior 416. Support base 434 can be, for example, a surface within a cell culture vessel/bioreactor (e.g., an interior surface of walls 104, FIG. 1), a cell culture vessel/bioreactor component such as coupler 544 (see FIGS. 5b, 6b) or coupler 532 (FIG. 6a), or a component that can be removably positioned within a cell culture vessel/bioreactor, such as axis 548 (FIG. 5d). In some examples, support base 434 may be a component coupled to axis 548, such as a plate or disc (see e.g., FIGS. 11a-12d). Support base 434 may also be a removable modular element for moving support assembly 400 from one process step to another. Coupler 432, disposed through support base 434 (shown by a broken line), may couple fluid conduit 420 to the interior of sealed chamber 416. Coupler 432 can be or include an outlet and/or aperture and may form a passage though support base 434, such as a threaded aperture configured to be coupled to a portion of fluid conduit 420. Alternatively, coupler 432 can include any mechanical element known in the art for use in coupling a fluid conduit to a receptacle, such as a nozzle, a gasket, an adhesive, or an adapter. In some examples, coupler 432 can be a stainless steel passage through support base 434 with a threaded end configured to couple to a corresponding end of fluid conduit 420. In some examples, coupler 432 may instead be coupled to elastic support 410 and may form a passage through elastic support 410 through which fluid may be added or removed from the interior of sealed chamber 416.

As shown in FIG. 4b, fluid may be forced through fluid conduit 420 and coupler 432 in the direction shown by the arrow. As the fluid enters and fills the interior of sealed chamber 416, the increase in fluid pressure may cause elastic support 410 to inflate, expanding outwardly. Cells 472 may be added to the cell culture vessel with a liquid growth medium to promote cell attachment and proliferation across elastic support 410.

FIG. 4c shows inflated elastic support 410 with a layer 474 of cells adhered to its outer surface. While layer 474 is shown as a monolayer for illustrative purposes, it is to be understood that layer 474 may include multiple cellular layers (e.g., a tissue). When the cells have reached the desired stage of growth/proliferation, fluid may be removed from the interior of sealed chamber 416 through coupler 432 and fluid conduit 420 in the direction shown by the arrow. As shown in FIG. 4d, the release of fluid pressure may cause elastic support 410 to deflate/contract, altering the surface and resulting in the mechanical detachment of the adherent cells. Cells exhibiting sufficient tensile strength and/or sufficient ECM development may detach from elastic support 410 in one or more sheets/groups, (e.g., layer 474). For example, layer 474 may include multiple layers of cells, and some or all of layer 474 may detach from elastic support 410 as a multi-layer sheet of cells. In some examples, the detached sheet of cells may have a three-dimensional configuration on elastic support 410 and may retain that configuration after detaching from elastic support 410. Other cells may detach from elastic support 410 as individual cells 472 or agglomerates thereof.

Removal of the fluid from sealed chamber 416 may be accomplished rapidly, causing a correspondingly rapid contraction of elastic support 410. This may be done, for example, by rapid pumping or venting of the fluid from sealed chamber 416. This may be accomplished with a hydraulic or pneumatic pump, by venting a pressurized reservoir, actuating a mechanical pressurizing device, and/or by the linear motion of the plunger of a syringe pump as described above. The deflation may be done in milliseconds to produce in significant dynamic mechanical separation forces. Changing the shape very quickly may lead to better results due to the inertia of the grown cells.

Alternatively, cells may be mechanically removed by further inflating elastic support 410, with or without deflation. In one example, elastic support 410 may be inflated and deflated in repeated cycles to mechanically remove the adhered cells as described above. In another example, cells may be grown on elastic support 410 in a relaxed configuration, and elastic support 410 may be rapidly inflated to mechanically remove the cells. In still another example, additional fluid pressure may be applied to elastic support 410 in the inflated configuration to cause the rupture of elastic support 410. This may produce an especially rapid contraction of elastic support 410 and promote mechanical removal of the adhered cells.

One or more elastic supports may be disposed within a cell culture vessel in any suitable arrangement. FIGS. 5a-5d illustrate sectional views of another illustrative embodiment of a cell culture vessel including elastic supports. FIGS. 6a-6d illustrate sectional views of the cell culture vessels of FIGS. 5a-5d taken along lines X-X. While the illustrated cell culture vessels have a cylindrical shape, other cell culture vessel shapes are also contemplated (e.g., square, rectangular, ovoid, spherical, columnar, etc.; see also FIGS. 9a-9d). Cells may be grown on any surface of the elastic supports shown. For example, if the cells are to be grown in spaces 516, spaces 516 may be filled with air, cellular growth medium, or other substance at atmospheric pressure, and the pressure within the interior of the cell culture vessel may be reduced to a pressure lower than atmospheric pressure.

As shown in FIGS. 5a, 5c, 6a, and 6c, an elastic support 510 may be coupled along its outer perimeter to an interior surface of culture vessel side wall 504. Elastic support 501 and side wall 504 may enclose space 516, which may be operatively coupled to a fluid source (see e.g., FIGS. 4a-4d). The interior surface of space 516 is shown lightly shaded where the section passes through elastic support 510.

Figure 6C:
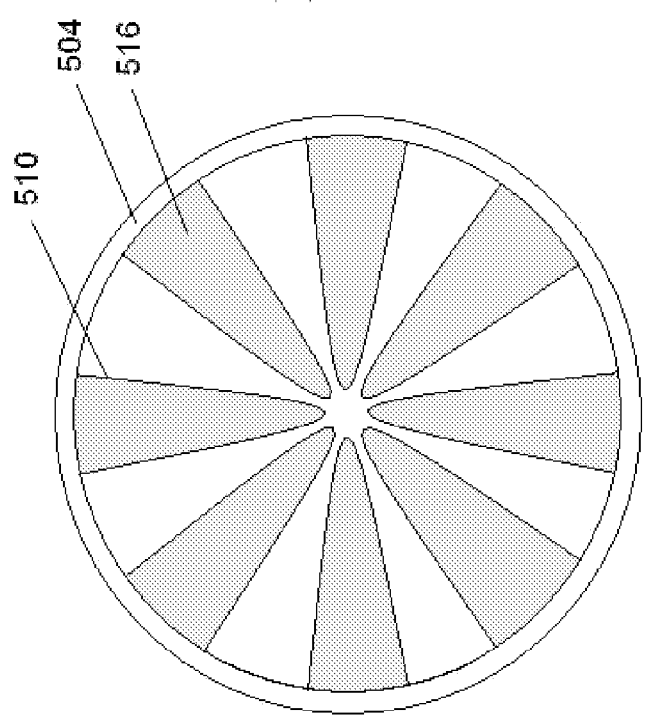
Figure 6D:
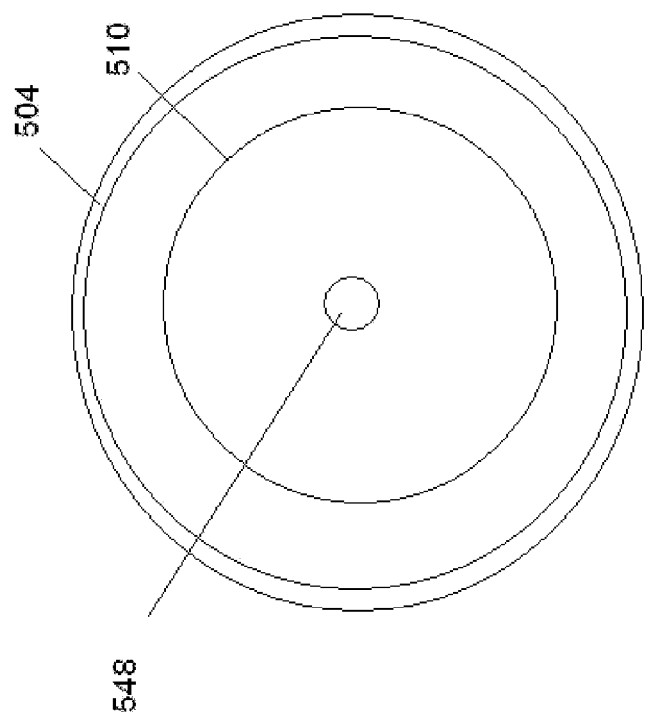

As shown in FIG. 6a, one or more elastic supports 510 may be coupled to one or more side walls 504 to create space 516. Fluid from a fluid source may be added or removed from space 516 through couplers 532. Alternatively, as shown in FIGS. 5b and 6b, one or more elastic supports 510 may be indirectly coupled to culture vessel side wall 504 by one or more couplers 544. Axis 546 may supply fluid, support one or more sensors, circulate fluid, and/or provide an axis of rotation for the culture vessel. Couplers 544 may extend through the culture vessel side wall 504 and may be coupled to a fluid conduit and/or fluid source. As shown in FIGS. 5d and 6d, one or more elastic supports 510 may be coupled to an axis 548 extending through at least some portion of the interior of a cell culture vessel. Axis 548 may be configured to rotate, and/or may be removable from the cell culture vessel.

One or more of a plurality of elastic supports 510 may be individually inflatable/deflatable. For example, each elastic support 510 may be coupled to a corresponding pressure control valve along axis 548. As pressurized fluid is supplied to axis 548, the pressure control valves may be individually controlled (e.g., by a controller and/or computing system) to inflate, deflate, and/or adjust the fluid pressure within each corresponding elastic support 510.

Figure 7:
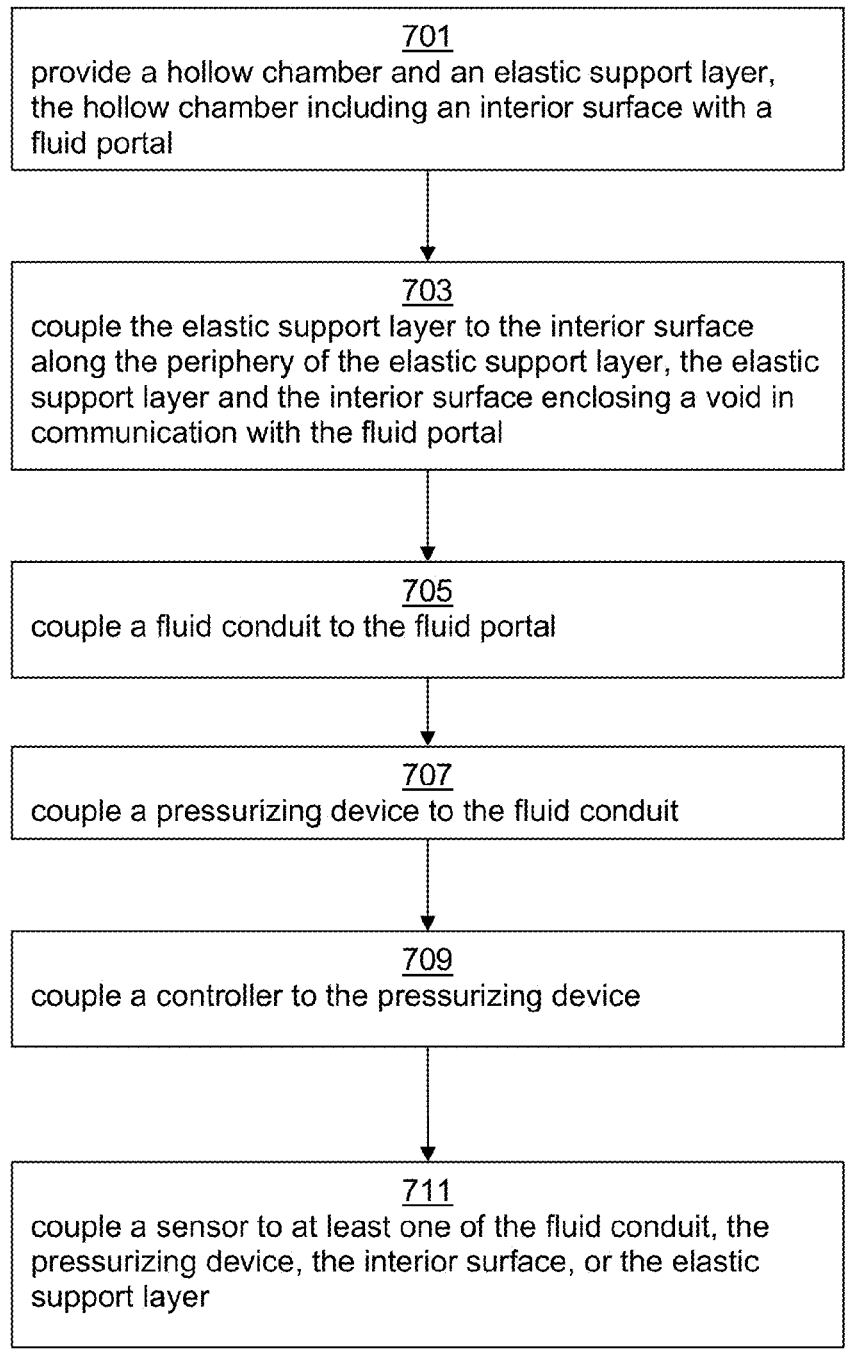
FIG. 7 shows a flow chart of a method for manufacturing a cell culture vessel with an elastic support.

FIG. 7 illustrates a flow chart for an illustrative embodiment of a method of manufacturing a cell culture vessel with an elastic support. It will also be appreciated that in some examples various blocks may be eliminated, divided into additional blocks, and/or combined with other blocks. Method 700 may begin at block 701.

At block 701, a hollow chamber and an elastic support may be provided. The hollow chamber may include an interior surface with a fluid portal. As described above, a fluid portal may be operatively coupled to the interior surface of a hollow chamber, such as a cell culture vessel.

At block 703, the elastic support may be coupled to the interior surface of the hollow chamber. The elastic support and the interior surface may enclose a void in communication with the fluid portal. As described above, the elastic support may be coupled to an interior surface with a mechanical fastener, an adhesive, a gasket, or any suitable coupling element/coupler.

At block 705, a fluid conduit may be coupled to the fluid portal. At block 707, a pressurizing device (e.g., a fluid pump) may be coupled to the fluid conduit. Some embodiments may lack a block 705/707. For example, one or more devices may be coupled to the elastic support layer and used to inflate/deflate the elastic support by mechanical pulling or stretching, rather than by fluid pressure.

At block 709, a controller may be coupled to the pressurizing device. As discussed above, a controller may be configured to automatically control a pressurizing/tensioning device in response to sensor input. Alternatively, a controller may be configured for manual operation of the pressurizing/tensioning device. The controller may send a command to the pressurizing/tensioning device to cause a sudden, rapid inflation or deflation of the elastic support.

At block 711, a sensor may be coupled to at least one of the fluid conduit, the pressurizing device, the interior surface, or the elastic support. In one example, a pressure sensor may be coupled to the elastic support and to the controller, and the controller may adjust the inflation/deflation of the elastic support in accordance with data received from the pressure sensor. In another example, a pressure sensor may be coupled to an interior wall of the hollow chamber, to the fluid conduit, and/or to the pressurizing device. In still other examples, the sensor may be or include an optical sensor, a strain sensor, a temperature sensor, a pH sensor, a biological molecule sensor, or other sensor as described above. A sensor may include a strain sensor embedded within the elastic support. Two or more sensors may be disposed in two or more locations, such as within the pressurizing device (e.g., a pressure sensor) and within the hollow chamber (e.g., an optical sensor). Alternatively, the hollow chamber may be constructed of glass or a transparent polymer, and an optical sensor may be disposed outside of the hollow chamber to monitor inflation/deflation of the elastic support.

FIG. 8 illustrates a flow chart for an illustrative embodiment of a method of culturing adherent cells on an elastic support. It will also be appreciated that in some examples various blocks may be eliminated, divided into additional blocks, and/or combined with other blocks. Method 800 may begin at block 801.

At block 801, an elastic support may be coupled to a surface within a cell culture vessel to form a chamber with an interior cavity. The elastic support may be coupled to the surface with a mechanical fastener, an adhesive, a gasket, and/or another suitable coupling element/coupler as described above.

At block 803, the interior cavity may be inflated by adding a fluid, such as a liquid growth medium and/or a gas, to the interior cavity. Alternatively, the interior cavity may be inflated by pulling/tensioning the elastic support mechanically, such as with a piston or other apparatus.

At block 805, cells may be added to the cell culture vessel. The cells may be added with a liquid medium, such as a cell growth medium, which may completely or partially cover the elastic support.

At block 807, the cells may be incubated within the culture vessel. As shown in FIG. 4c, cells may adhere to one or more surface portions of the elastic support and may proliferate across the surface. Incubating the cells may include monitoring and adjusting environmental parameters such as carbon dioxide, oxygen, temperature, waste product concentration, nutrient concentration, etc. In addition, incubating the cells may include removing liquid medium from the cell culture vessel and rinsing the elastic support to remove non-viable cells and debris. More medium may then be added to the cell culture vessel.

At block 809, a sensor may sense one or more of pressure, temperature, oxygen or carbon dioxide concentration, strain, position, geometry, and analyte concentration within the cell culture vessel. The sensor may send feedback to a controller, and based on the feedback, the controller may send a command to a displacement device to alter the configuration of the elastic support. A displacement device (e.g., a fluid pump/pressurizer, a mechanical tensioning device, etc.) may be automatically controlled by the controller to alter the configuration of the elastic support. The command may be sent in response to sensor data received by the controller, in response to a manually entered command, and/or in response to lapse of a predetermined length of time.

At block 811, the configuration of the elastic support may be altered to detach the cells from the elastic support. The configuration of the elastic support may be altered by applying/releasing tension or fluid pressure against the elastic support. The application/release of tension or fluid pressure may be done rapidly, such as by a pneumatic or hydraulic device, in order to rapidly alter the configuration of the elastic support and promote cell detachment. The configuration of the elastic support may be altered, for example, in response to feedback from a sensor. Cells may be removed in groups, in a sheet or other structure (e.g., a monolayer, a tissue, or a multiple cell layer structure), and/or as individual cells. In some examples, cells may form a sheet or other structure with a three-dimensional configuration on the elastic support, and the sheet or other structure may fully or partially retain the three-dimensional configuration after detaching from the elastic support.

At block 813, the detached cells may be collected. After the cells have been detached from the elastic support, the cells may be recovered using any suitable technique known in the art, such as by flow cytometry, centrifugation, or other recovery method. In one example, a cell collection apparatus may be coupled to the cell culture vessel to collect cells from liquid medium drained or pumped from the cell culture vessel.

Figure 9A:
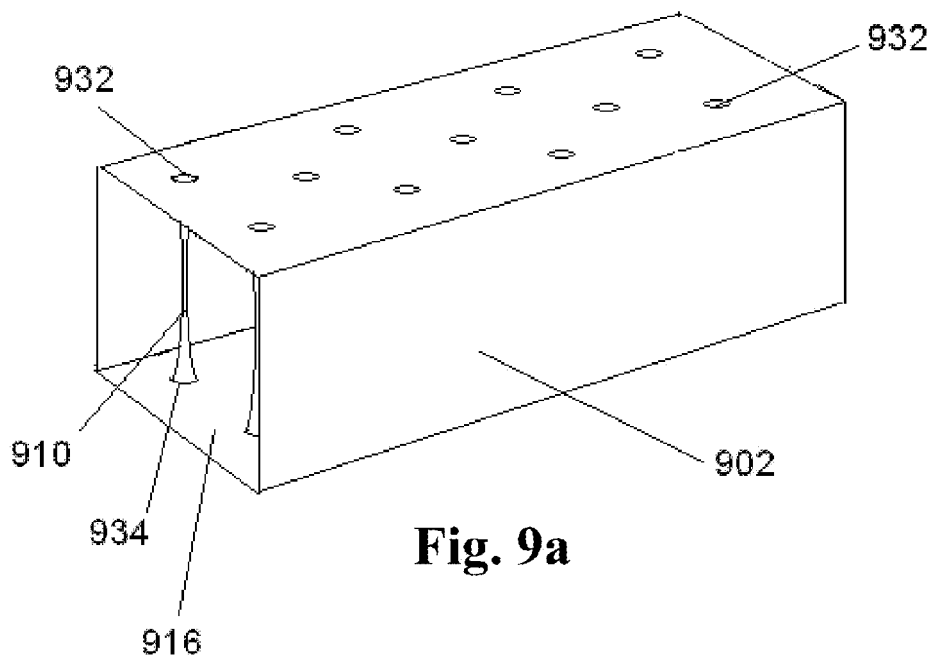
FIGS. 9a-9d illustrate perspective views of a rectangular cell culture vessel with a plurality of elastic supports arranged in parallel.
Figure 9B:
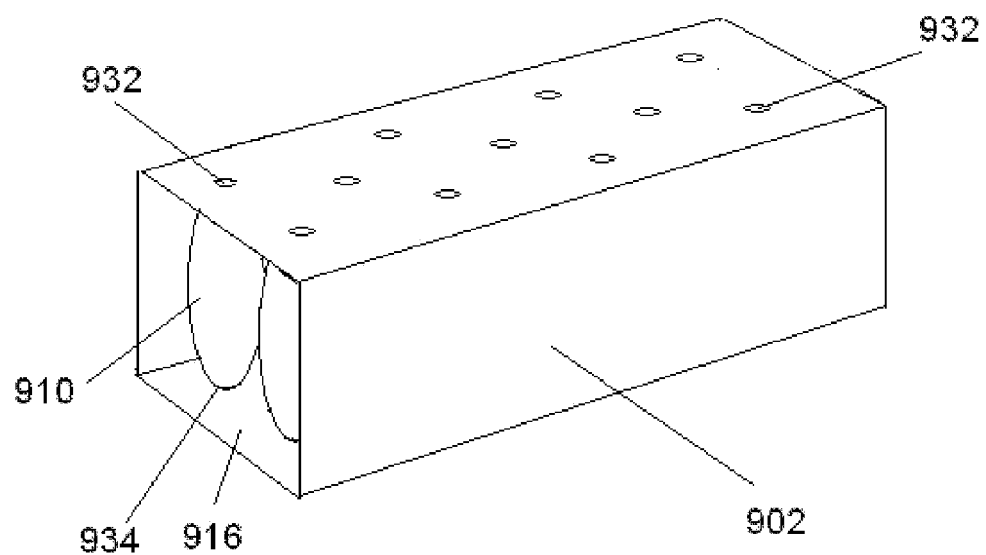

Elastic supports may be used with a variety of cell culture vessels/chambers in any suitable configuration. FIGS. 9a-9d illustrate perspective views of an illustrative embodiment of a rectangular cell culture vessel with a plurality of elastic supports arranged in parallel. As shown in FIGS. 9a-9b, a cell culture vessel may include elastic supports 910 coupled at one end to coupler 932 and coupled at the opposite end to coupler 934. The cell culture vessel may further include side walls 902 and an interior surface 916. FIG. 9a shows elastic supports 910 in a relaxed configuration, while FIG. 9b shows elastic supports 910 in an inflated configuration.

Cell culture vessels with elastic supports may be stackable/couplable to one another. For example, one cell culture vessel may be placed on another cell culture vessel such that coupler 932 and coupler 934 on the cell culture vessels may interlock or otherwise interface to provide a continuous fluid flow path through consecutive elastic supports 910 in the stacked cell culture vessels. For example, a bioreactor may include a stack or series of cell culture vessels as shown in FIGS. 9a-9d. In some embodiments, a series or stack of coupled cell culture vessels may be controlled by a single controller.

Each cell culture vessel of the series/stack may be independently controlled. For example, each of the cell culture vessels may have a separate pressure control valve coupled to the same fluid source (e.g., through a shared plenum or conduit). Alternatively, the cell culture vessels may be coupled to different fluid sources or to independently controlled/pressurized plenums or conduits connected to the same fluid source. The controller may send commands to an individual pressure control valve, fluid source, or independently controlled/pressurized plenum or conduit in order to differentially control inflation/deflation of elastic supports within each cell culture vessel.

In another example, one or more of the elastic supports of each vessel may have corresponding individual pressure control valves and may be independently controlled within one or more cell culture vessels. In still other examples, the elastic supports and/or cell culture vessels of the series/stack may be controlled as a single unit. This may be achieved by coupling each of the elastic supports and/or cell culture vessels to a common fluid source without separate pressure control valves, or by synchronizing the operations of individual pressure control valves.

Figure 9C:
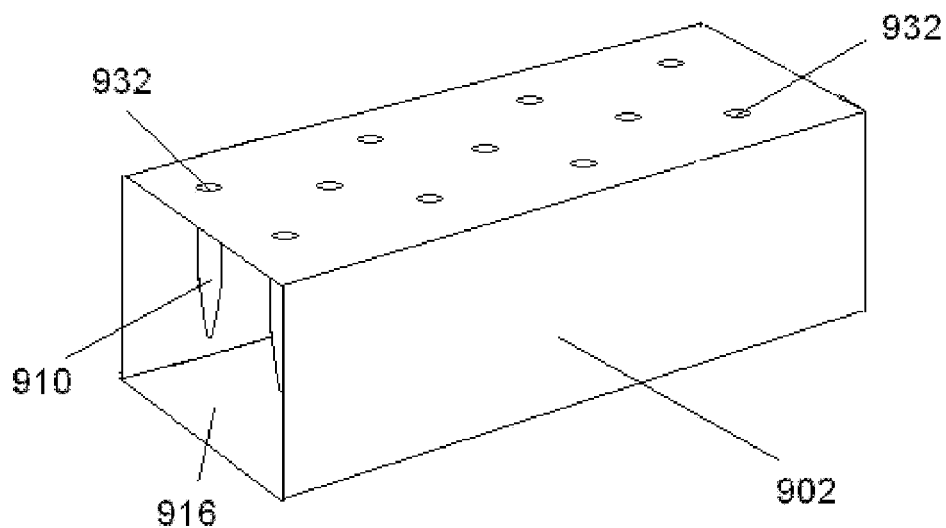
Figure 9D:
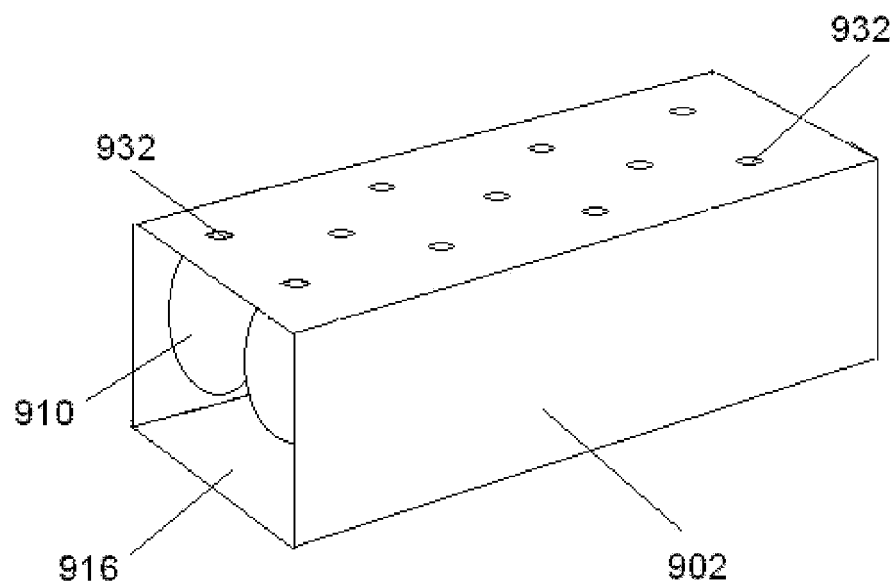

As shown in FIGS. 9c-9d, elastic supports 910 may be coupled at only one end to the cell culture vessel. FIG. 9c shows elastic supports 910 in a relaxed configuration, while FIG. 9d shows elastic supports 910 in an inflated configuration. While the cell culture vessels of FIGS. 9a-9d are shown with at least one open end, a cell culture vessel may further include end walls to completely enclose elastic supports 910.

Figure 10:
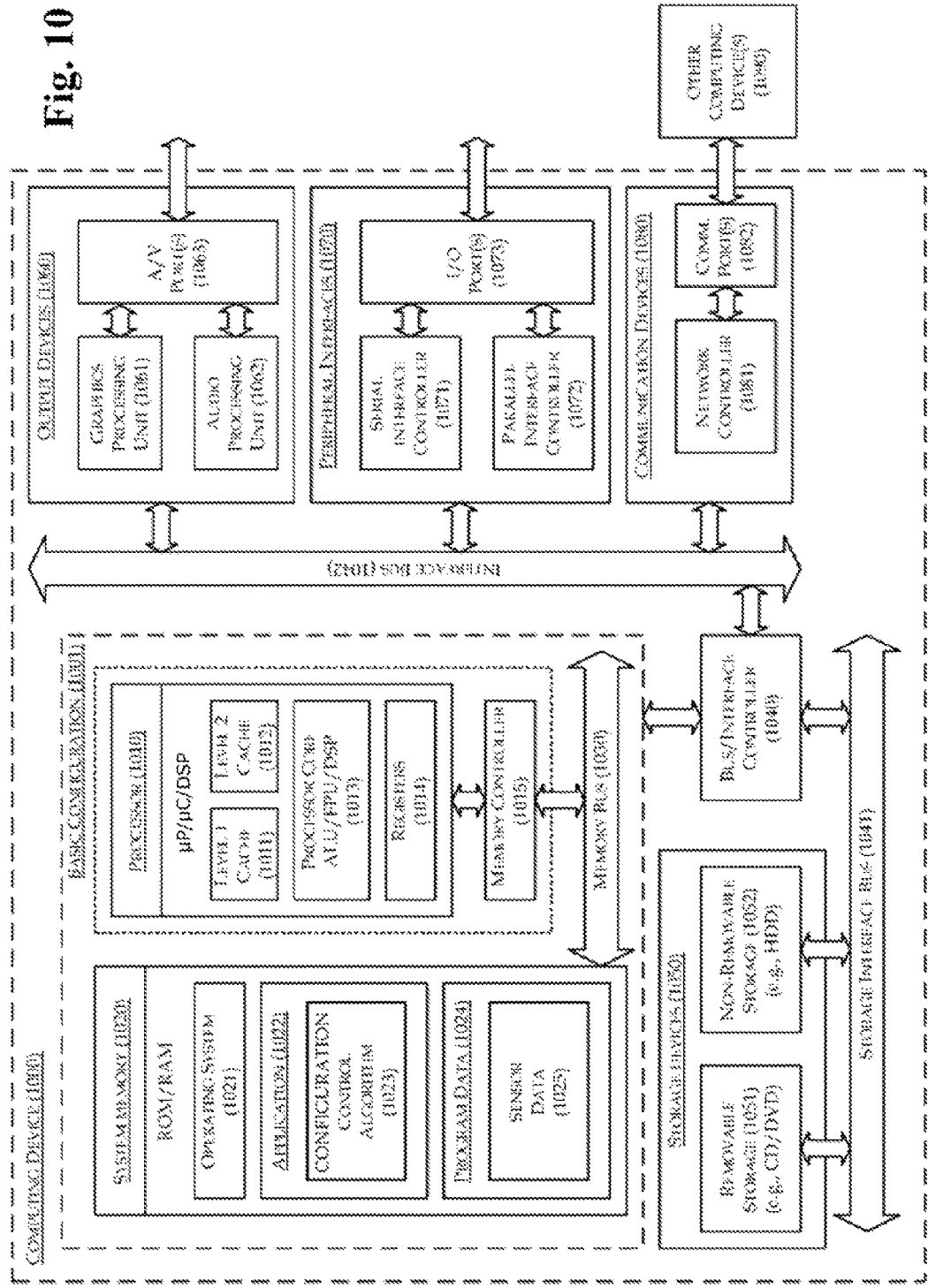
FIG. 10 shows a block diagram illustrating an example computing device arranged for controlling the configuration of an elastic cell support.

FIG. 10 is a block diagram illustrating an example computing device 1000 that is arranged for controlling the configuration of an elastic cell support in accordance with the present disclosure. In a very basic configuration 1001, computing device 1000 typically includes one or more processors 1010 and system memory 1020. A memory bus 1030 may be used for communicating between the processor 1010 and the system memory 1020.

Depending on the desired configuration, processor 1010 may be of any type including but not limited to a microprocessor (µP), a microcontroller (µC), a digital signal processor (DSP), or any combination thereof. Processor 1010 may include one more levels of caching, such as a level one cache 1011 and a level two cache 1012, a processor core 1013, and registers 1014. An example processor core 1013 may include an arithmetic logic unit (ALU), a floating point unit (FPU), a digital signal processing core (DSP Core), or any combination thereof. An example memory controller 1015 may also be used with the processor 1010, or in some implementations the memory controller 1015 may be an internal part of the processor 1010.

Depending on the desired configuration, the system memory 1020 may be of any type including but not limited to volatile memory (such as RAM), non-volatile memory (such as ROM, flash memory, etc.) or any combination thereof. System memory 1020 may include an operating system 1021, one or more applications 1022, and program data 1024. Application 1022 may include a configuration control algorithm 1023 that is arranged to generate a command to control the configuration of an elastic cell support (e.g., to generate a command to fluid displacement device 130 to increase or decrease fluid pressure within sealed chamber 116; see FIG. 1). Program Data 1024 includes sensor data 1025 that is useful for controlling the configuration of the elastic cell support. In some embodiments, application 1022 may be arranged to operate with program data 1024 on an operating system 1021 such that tension/pressure on the elastic cell support is adjusted based on the sensed parameter(s). For example, sensor data 1025 may include a measure of the concentration of an analyte in a liquid cell culture medium. The concentration of the analyte in the cell culture medium may be proportional to the number of cells exposed to the medium, and a command to abruptly decrease tension/pressure applied to the elastic cell support to release the cells may be generated in response to the analyte reaching a predetermined concentration. This described basic configuration is illustrated in FIG. 10 by those components within dashed line 1001.

Computing device 1000 may have additional features or functionality, and additional interfaces to facilitate communications between the basic configuration 1001 and any required devices and interfaces. For example, a bus/interface controller 1040 may be used to facilitate communications between the basic configuration 1001 and one or more data storage devices 1050 via a storage interface bus 1041. The data storage devices 1050 may be removable storage devices 1051, non-removable storage devices 1052, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 1020, removable storage 1051 and non-removable storage 1052 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 1000. Any such computer storage media may be part of computing device 1000.

Computing device 1000 may also include an interface bus 1042 for facilitating communication from various interface devices (e.g., output interfaces, peripheral interfaces, and communication interfaces) to the basic configuration 1001 via the bus/interface controller 1040. Example output devices 1060 include a graphics processing unit 1061 and an audio processing unit 1062, which may be configured to communicate to various external devices such as a display or speakers via one or more A/V ports 1063. Example peripheral interfaces 1070 include a serial interface controller 1071 or a parallel interface controller 1072, which may be configured to communicate with external devices such as input devices (e.g., keyboard, mouse, pen, voice input device, touch input device, etc.) or other peripheral devices (e.g., printer, scanner, etc.) via one or more I/O ports 1073. An example communication device 1080 includes a network controller 1081, which may be arranged to facilitate communications with one or more other computing devices 1090 over a network communication link via one or more communication ports 1082.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 1000 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 1000 may also be implemented as a personal computer including both laptop computer and non-laptop computer configurations.

As discussed above, an elastic support may be coupled to an interior surface of a cell culture vessel, such as an inner wall of the cell culture vessel, a support base, and/or an axis within a cell culture vessel (see e.g., FIGS. 1, 4a-4d, and 5d). FIGS. 11a-12d illustrate examples of support bases and other articles configured for use with one or more elastic supports. In these examples, the support base is a rotatable disc with a center annulus. The rotatable disc can be constructed from any rigid or semi-rigid material, such as metal or plastic. The rotatable disc has a concave top surface and either a concave bottom surface ("double-sided" rotatable disc) or a flat/non-concave bottom surface ("single-sided" rotatable disc). An annular elastic support is coupled along its inner periphery and/or outer periphery to the rotatable disc at the center annulus and/or outer periphery, leaving a void between the elastic support and the concave top or bottom surface of the rotatable disc. One or more internal passages within the rotatable disc connect the center annulus and the void. These passages can be coupled to a fluid conduit disposed through the center annulus of the rotatable disc(s). Fluid can be supplied to, or withdrawn from, the void (via the fluid conduit and passages) to inflate and deflate the elastic support. One or more valves may be provided within the passages to control fluid flow.

Figures 11A, 11B:
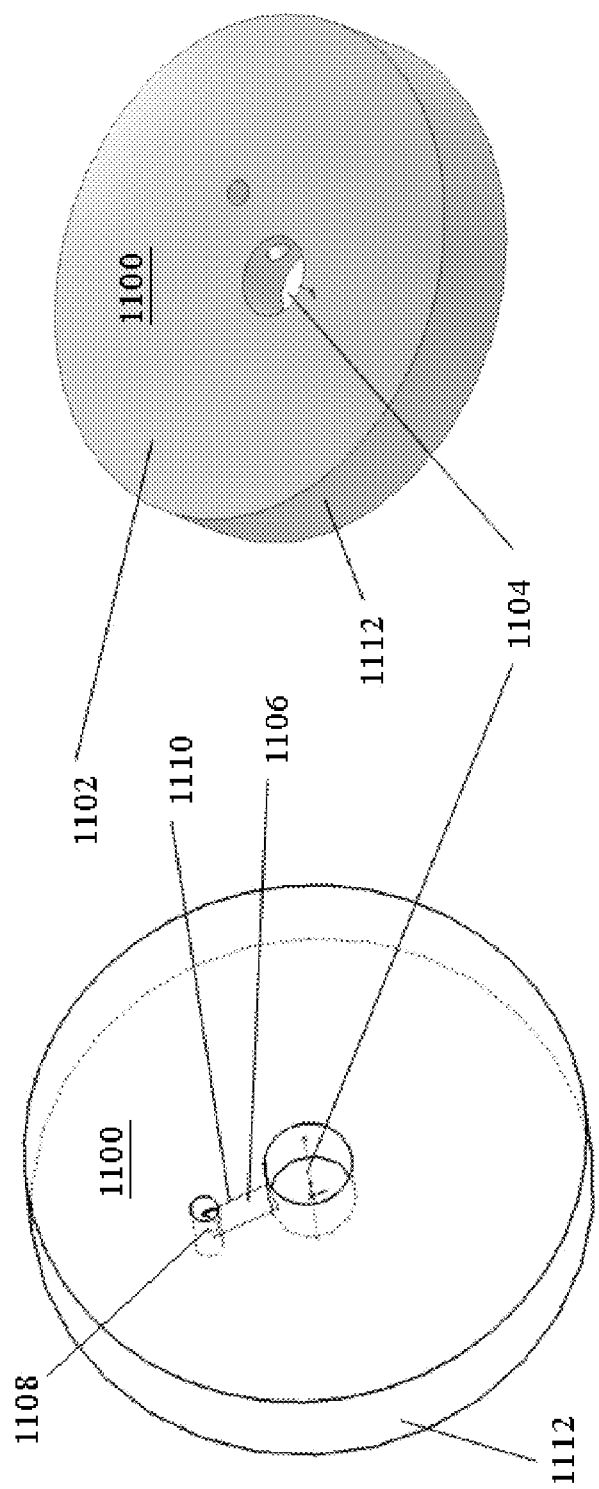
FIGS. 11a-11k illustrate examples of a support base configured for use with an elastic support.
Figure 11C:
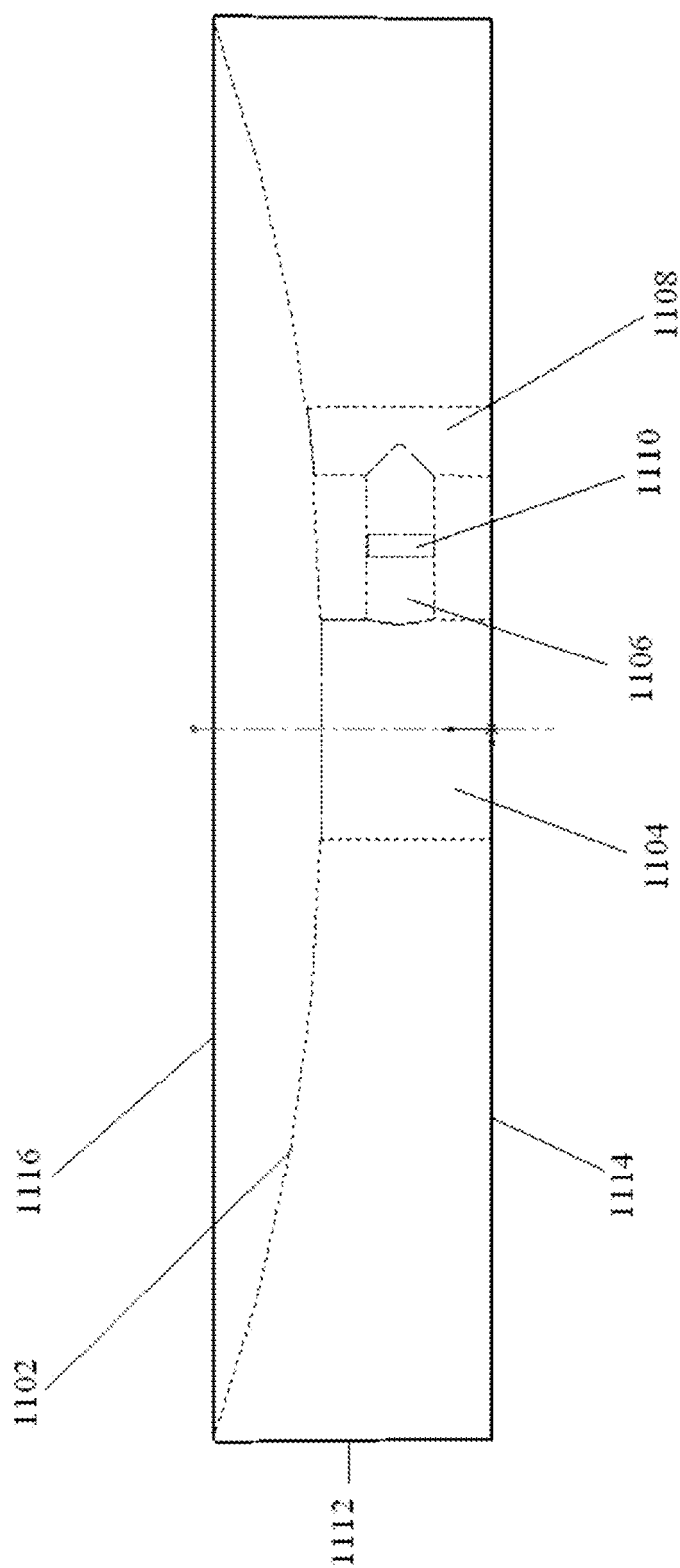

Examples of single-sided rotatable discs are illustrated in FIGS. 11a-11g. As shown in FIGS. 11a, 11b, and 11c, rotatable disc 1100 may have top 1102, bottom 1114, and side(s) 1112. As best viewed in FIG. 11c, top 1102 is concave. Thus, rotatable disc 1100 may be thickest along side 1112 and thinnest at the edges of conduit aperture 1104. Fluid conduit aperture 1104 may pass through rotatable disc 1100 and may be in fluid communication with first passage 1106, which extends laterally within rotatable disc 1100. First passage 1106 may be coupled to second passage 1108, which may have an opening continuous with top 1102. As shown in FIG. 11*c*, first passage 1106 may include one or more valve(s) 1110, which may be actuable (e.g., electronically and/or remotely) to control fluid flow. Alternatively, valve 1110 may be provided in second passage 1108.

In the illustrated example, rotatable disc 1100 has a diameter of 20 cm with a thickness of 3 cm at fluid conduit aperture 1104. Fluid conduit aperture 1104 is 3 cm in diameter, and the distance between the center of second passage 1108 and the center of fluid conduit aperture 1104 is 3 cm. These dimensions are provided merely as an example and are not intended to be limiting. Rotatable discs or other support bases configured for use with an elastic support may vary in size, thickness, and configuration according to intended use. For example, one or more dimensions may be altered to adapt a rotatable disc or other support base for use with various commercially available cell culture devices/systems.

Figure 11D:
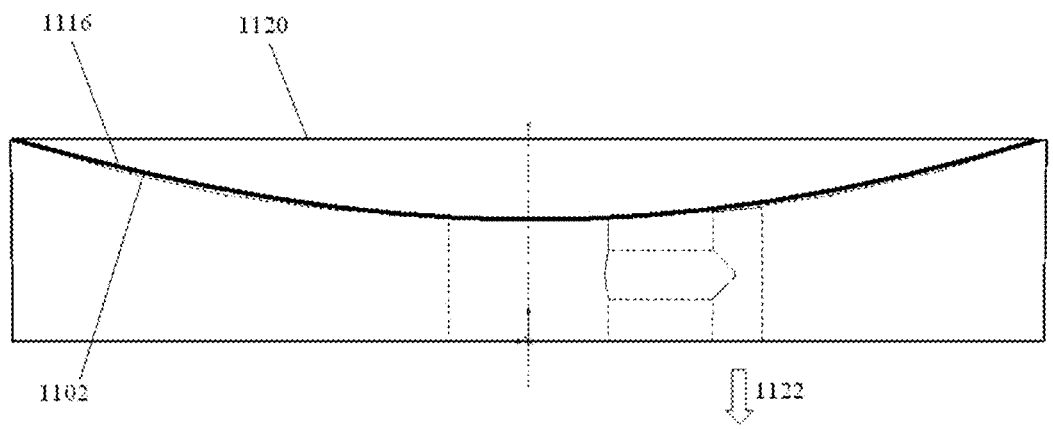
Figure 11E:
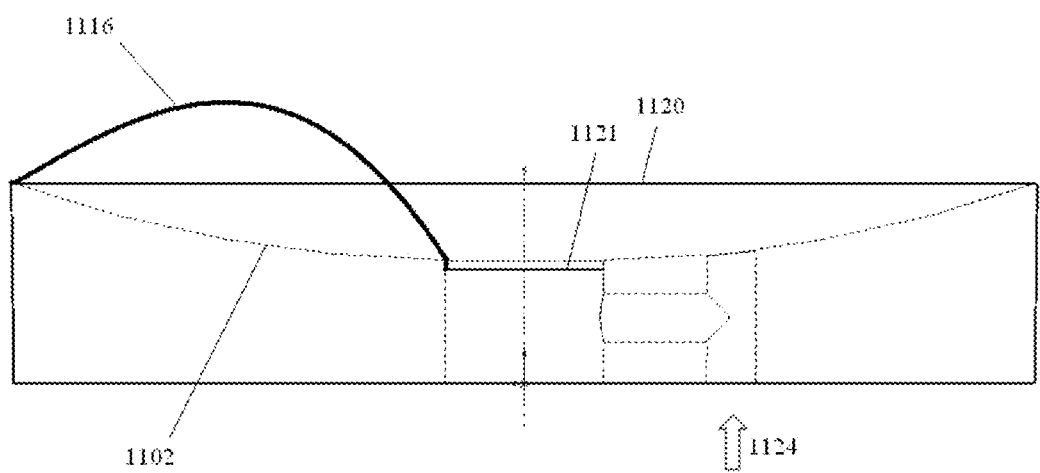

Referring now to FIGS. 11*c*, 11*d*, and 11*e*, elastic support 1116 is coupled to the exterior of rotatable disc 1100. In this example, elastic support 1116 is an annular polytetrafluoroethylene sheet with a diameter of 20 cm, a central annulus with a diameter of 3 cm, and an annular textured surface portion designed to encourage cell anchoring/adhesion. The annular textured surface portion begins at a radius of 5 cm from the center of the central annulus. The annular textured surface portion may extend along an annular mid span portion of elastic support 1116, and may be flanked by annular non-textured surface portions around the central annulus and/or around the outer periphery of elastic support 1116. The textured surface can be, for example, a rectangular array of molded cylindrical nubs, with each nub measuring 0.3 μm in width or diameter and 2 μm in height.

As best shown by FIG. 11*e*, elastic support 1116 may be coupled to rotatable disc 1100 around the periphery of top 1102 by fastener 1120 disposed along side 1112. Elastic support 1116 may be coupled to top 1102 by fastener 1121 disposed within fluid conduit aperture 1104 (FIG. 11*e*). In the illustrated example, the fasteners are ring clamps. However, as described in detail above, other fasteners may be used to couple elastic support 1116 to rotatable disc 1100. In some examples, fastener 1120 may be coupled to a fluid conduit such as fluid conduit 1226 (see FIG. 12*d*; see also FIG. 11*j*).

Figure 11F:
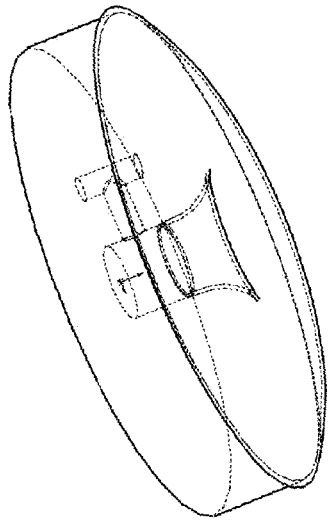
Figure 11G:
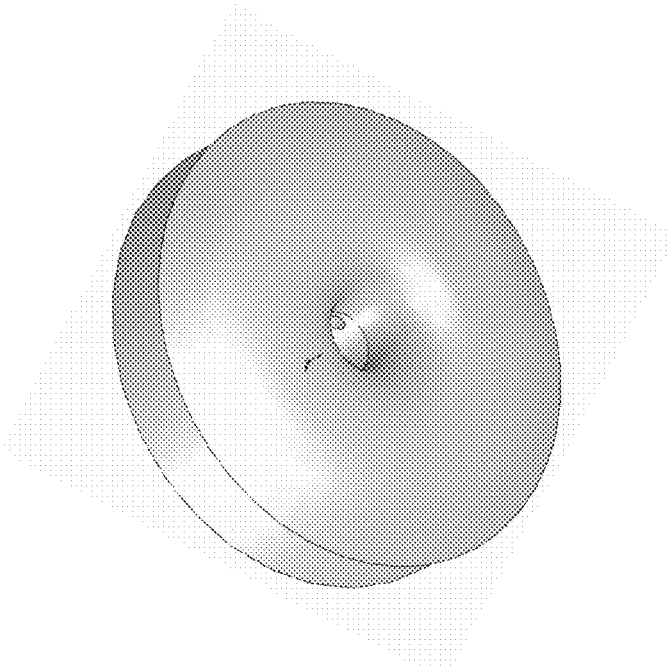

The fluid conduit may be coupled to a fluid displacement device (see e.g., FIG. 1, fluid displacement device 130). The fluid displacement device may be operated to draw fluid from the fluid conduit, causing fluid between elastic support 1116 and top 1102 to flow through second passage 1108 and first passage 1106 toward the fluid conduit. As shown in FIG. 11*d*, removal of fluid through second passage 1108 in the direction indicated (Arrow 1122) may pull elastic support 1116 toward the concave surface of top 1102 (deflation). The fluid displacement device may also be operated to add fluid to the fluid conduit, causing fluid to flow from the fluid conduit through first passage 1106, second passage 1108, and into the space between top 1102 and elastic support 1116. As shown in FIG. 11*e*, addition of fluid between top 1102 and elastic support 1116 through second passage 1108 in the direction indicated (Arrow 1124) may cause outward expansion (inflation) of elastic support 1116. FIGS. 11*f* and 11*g* show additional views of rotatable disc 1100 with elastic support 1116 in an inflated configuration.

Figure 11H:
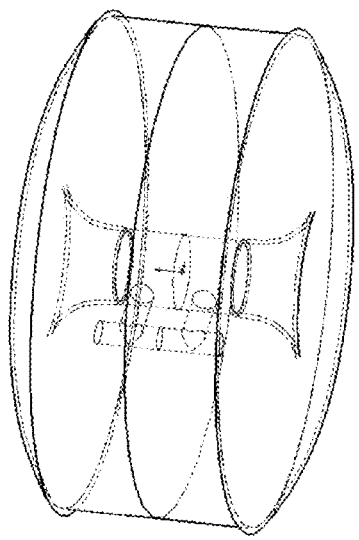
Figure 11I:
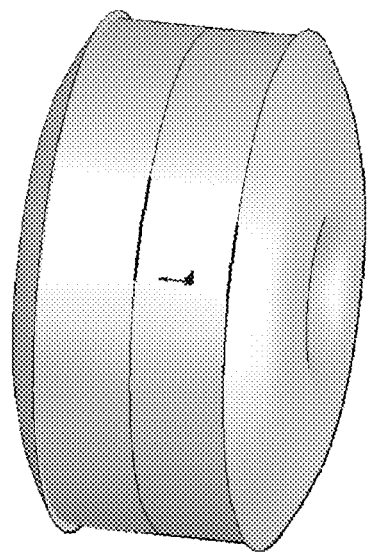
Figure 11J:
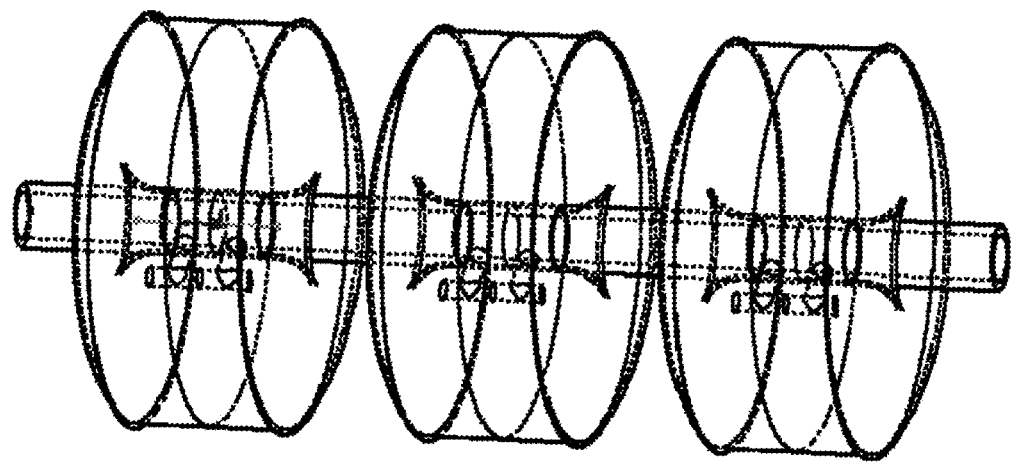
Figure 11K:
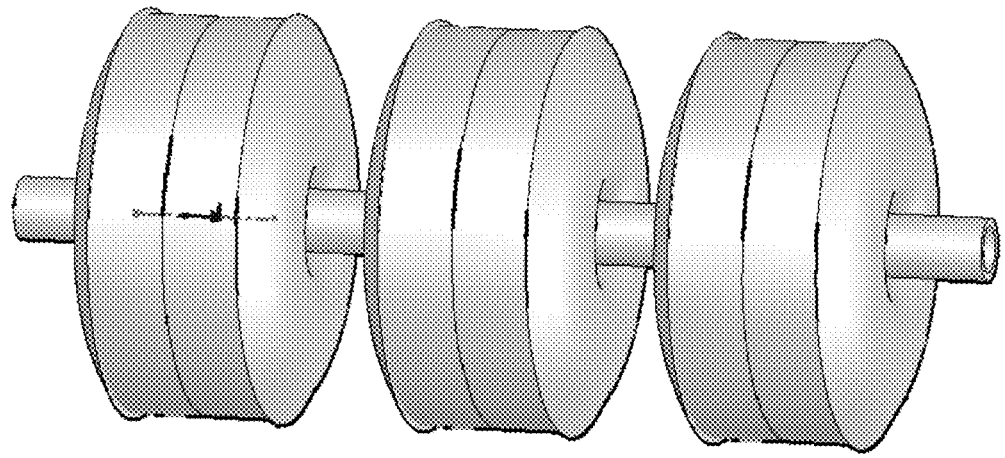

Optionally, as illustrated in FIGS. 11*h* and 11*i*, two rotatable discs 1100 with elastic supports 1116 may be coupled along bottoms 1114 of the rotatable discs. The coupled rotatable discs may share a common fluid source that passes through fluid conduit apertures 1104. First passages 1106 of the rotatable discs may be connected, allowing inflation/deflation of both elastic supports 1116 simultaneously. In addition, valves 1110 and/or a valve between first passages 1106 may allow differential inflation/deflation of elastic supports 1116. In some examples, a valve or seal may be included between the respective first passages 1106 to allow control of each elastic support separately. As illustrated in FIGS. 11*j* and 11*k*, three such pairs of rotatable discs may be arrayed along a common fluid conduit that passes through fluid conduit apertures 1104 of each pair. In other examples, one, two, or more than three pairs of rotatable discs may be arrayed on a fluid conduit.

Examples of double-sided rotatable discs configured for use with two elastic supports are illustrated in FIGS. 12*a*-12*d*. Like the single-sided rotatable disc 1100, the illustrated double-sided rotatable disc 1200 includes top 1202, side(s) 1212, fluid conduit aperture 1104, first passage 1206 with valve 1210, second passage 1208, and elastic support 1216. In addition, rotatable disc 1200 has third passage 1207, which is open to the bottom of rotatable disc 1200 and includes valve 1211. In some examples, a valve may also/instead be provided within second passage 1208. Rotatable disc 1200 also has bottom 1214, and both top 1202 and bottom 1214 are concave. Elastic support 1216 may be coupled to top 1202 and elastic support 1218 may be coupled to bottom 1214 in the manner described above. Alternatively, elastic supports 1216 and 1218 may be formed as a single unit, which may be coupled to the rotatable disc with a single ring clamp disposed around the circumference of the rotatable disc (i.e., along side 1212) or within fluid conduit aperture 1204.

Figure 12A:
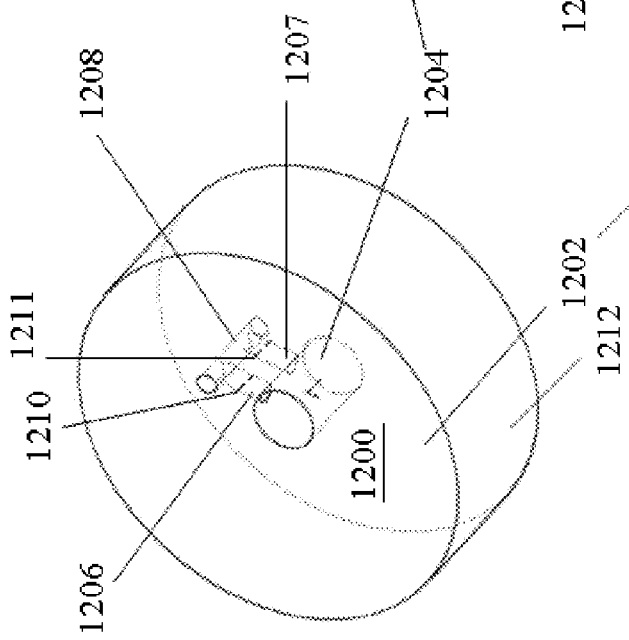
FIGS. 12a-12d illustrate examples of a support base configured for use with two elastic supports.
Figure 12B:
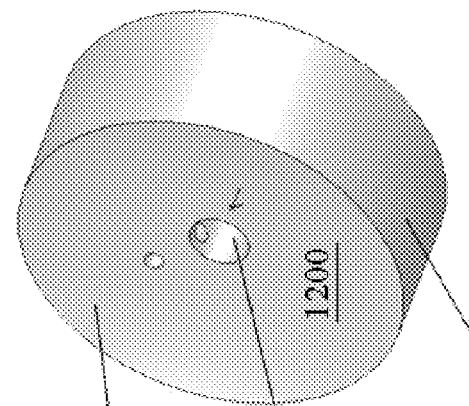
Figure 12C:
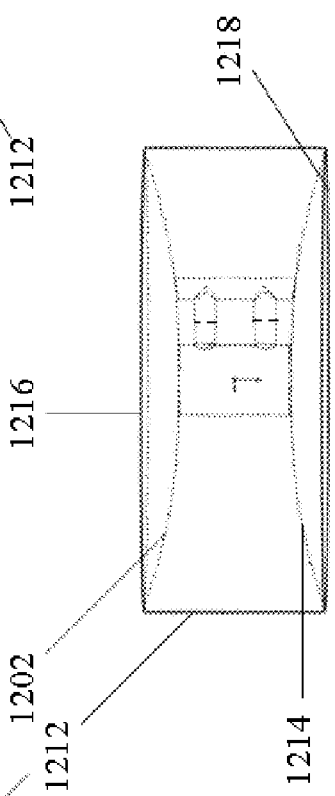
Figure 12D:
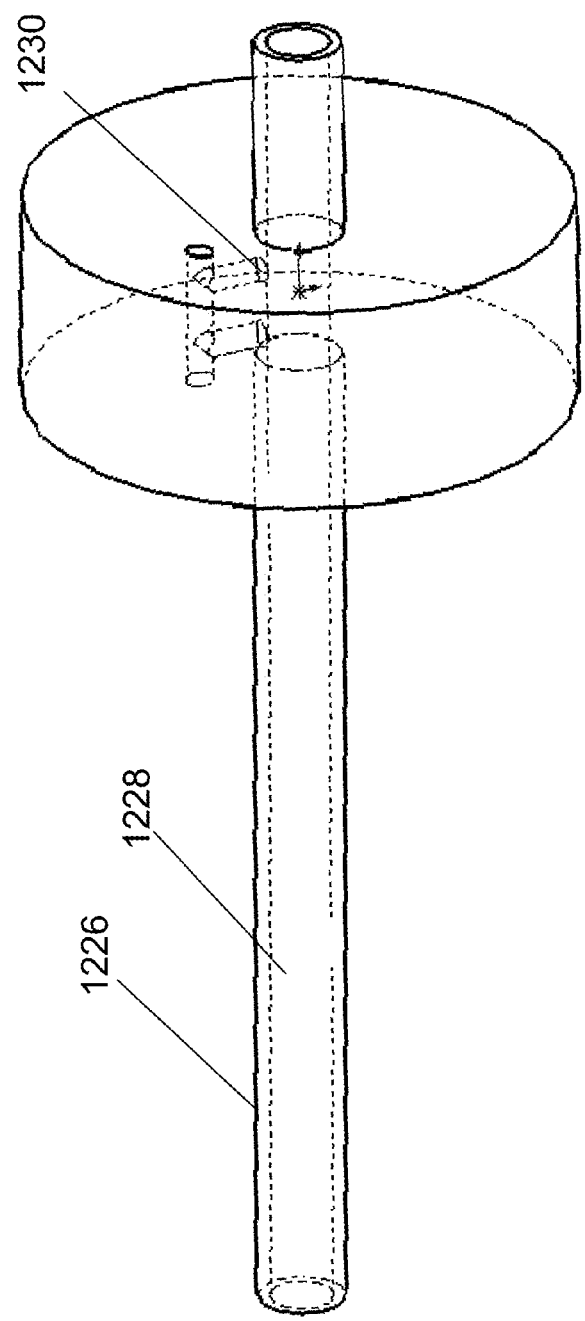

FIG. 12*d* illustrates a fluid conduit coupled to rotatable disc 1200. However, it is to be understood that a fluid conduit may be coupled in a similar manner to rotatable disc(s) 1100 illustrated in FIGS. 11*a*-11*k*. As shown, fluid conduit 1226 may be disposed through fluid conduit aperture 1204 of one or more rotatable discs 1200 (see also FIGS. 11*j* and 11*k*). Fluid conduit 1226 may be in fluid communication with first passage 1206, and with third passage 1207 if present, through portal(s) 1230. A fluid displacement device may be coupled to fluid conduit 1226 as further described above, and may supply fluid 1228 to fluid conduit 1226. Valves 1210 and 1211 may be variably controlled to permit differential or synchronous inflation/deflation of elastic supports 1216 and 1218. Fluid conduit 1226 may be coupled to a device that is configured to rotate rotatable disc(s) 1200, fluid conduit 1226, or both.

In operation, a fluid conduit (e.g., fluid conduit 1226) coupled to one or more single-sided or double-sided rotatable discs with elastic supports may be positioned within a cell culture vessel. For example, the fluid conduit may be positioned horizontally within the culture chamber of a rotating bed bioreactor such as the Z® RP Bioreactor (Zellwerk GmbH-HiPer-Gruppe). A fluid displacement device coupled to the fluid conduit may induce negative pressure (e.g., atmospheric pressure minus 10 psi) within the fluid conduit. One or more valves (e.g., valves 1110, 1210, 1211, etc.) within the passages of the rotatable discs may be opened to allow fluid passage. The negative pressure may hold the elastic supports against the concave tops and/or bottoms of the rotatable discs. Liquid cell culture medium may be added to the interior of the cell culture vessel in sufficient quantity to submerge approximately half of each of the rotatable discs. Cells may be added with the liquid cell culture medium or separately. The rotatable discs may then be rotated continuously or semi-continuously for a period of time to allow growth of the added cells on the elastic supports. For example, the rotatable discs may be rotated at the rate of 1 rotation per hour for 120 days.

To detach the adherent cells from the elastic supports, the cells may be removed from the liquid cell culture medium (e.g., by draining the liquid cell culture medium from the cell culture vessel). The fluid displacement device may apply alternating pressures within the fluid conduit at a frequency below the resonance frequency of the elastic supports. For example, applied pressures may alternate between atmospheric pressure plus 10 psi and atmospheric pressure minus 10 psi at 5 Hz. The alternating pressures may cause cyclical inflation and deflation of the elastic supports (i.e., inflation/deflation cycling), which may aid cell detachment from the elastic supports as described above. Optionally, individual valves within rotatable discs may be differentially controlled to alternate cycling among consecutive elastic supports. This alternation of cycling may reduce or prevent impacts between neighboring elastic supports and consequent damage to the adherent cells. A continuous or semi-continuous spray of liquid (e.g., buffered saline, liquid cell culture medium, or any isotonic liquid) may be applied to the elastic supports during and/or after the inflation/deflation cycling to help clean and collect cells as they detach. The elastic supports may be disposable. Alternatively, the elastic supports may be cleaned using any known method (e.g., by immersion and/or agitation in a solution including one or more of deionized water, a surfactant, and/or an enzyme) and reused.

The herein-described subject matter sometimes illustrates different components or elements contained within, coupled to, or connected with, different other components or elements. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or Figures, should be understood to contemplate the possibilities of including one of the terms, either of the terms, or both terms. For example, the phrase "A or B" will be understood to include the possibilities of "A" or "B" or "A and B."

Various operations may be described as multiple discrete operations in turn, in a manner that may be helpful in understanding embodiments; however, the order of description should not be construed to imply that these operations are order-dependent. Also, embodiments may have fewer operations than described. A description of multiple discrete operations should not be construed to imply that all operations are necessary. Also, embodiments may have fewer operations than described. A description of multiple discrete operations should not be construed to imply that all operations are necessary.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the disclosure. Those with skill in the art will readily appreciate that embodiments of the disclosure may be implemented in a very wide variety of ways. This disclosure is intended to cover any adaptations or variations of the embodiments discussed herein. Therefore, it is manifestly intended that embodiments of the disclosure be limited only by the claims and the equivalents thereof.

What is claimed is:

1. An annular dynamic adherent cell support comprising:
   an expandable elastic support layer with a first surface and a second surface, the expandable elastic support layer configured to assume a first configuration in response to a first applied tension or pressure and to assume a second configuration in response to a second applied tension or pressure, wherein the expandable elastic support layer comprises an annular shape defining a hole;
   an annular support base coupled to the expandable elastic support layer and comprising a first exterior portion, a tube, and an internal passage, wherein the internal passage connects the first exterior portion to the tube, wherein the first exterior portion of the annular support base and the second surface of the expandable elastic support layer at least partially define a void, wherein the internal passage extends between the tube and the void such that the void is in fluid communication with the internal passage, and wherein the tube is connected to the expandable elastic support layer at the hole of the expandable elastic support layer; and
   an aperture extending through the annular dynamic adherent cell support and through the expandable elastic support layer, wherein the aperture is defined by the hole of the expandable elastic support layer and the tube, and wherein the aperture is configured to receive a rotatable fluid conduit.

2. The annular dynamic adherent cell support of claim 1, further comprising a fastener continuously coupled to the expandable elastic support layer.

3. The annular dynamic adherent cell support of claim 1, wherein the elastic support layer further comprises an integrated inelastic material.

4. The annular dynamic adherent cell support of claim 1, wherein the first surface comprises one or more textured surface portions and one or more non-textured surface portions adjacent to the one or more textured surface portions.

5. The annular dynamic adherent cell support of claim 4, wherein the one or more textured surface portions comprises a hydrophobic coating or a hydrophilic coating.

6. The annular dynamic adherent cell support of claim 1, wherein the first configuration is a relaxed three-dimensional configuration and the second configuration is an expanded three-dimensional configuration, and wherein the elastic support layer is permeable to a component of a cell culture medium in the expanded three-dimensional configuration.

7. The annular dynamic adherent cell support of claim 6, wherein the elastic support layer further comprises a plurality of pores configured to expand in response to fluid pressure.

8. The annular dynamic adherent cell support of claim 1, wherein the annular support base comprises a rotatable annular support base.

9. The annular dynamic adherent cell support of claim 1, wherein the annular support base comprises a second internal passage in fluid communication with the first internal passage.

10. The annular dynamic adherent cell support of claim 9, wherein the annular support base further comprises a valve fluidly coupled between the first internal passage and the second internal passage.

11. The annular dynamic adherent cell support of claim 9, wherein a portion of the second internal passage extends laterally within the annular support base.

12. The annular dynamic adherent cell support of claim 1, wherein the expandable elastic support layer is coupled to the annular support base by a fastener disposed within the first internal passage.

13. The annular dynamic adherent cell support of claim 1, wherein the hole of the expandable elastic support layer has a diameter that is equal to a diameter of the tube, and wherein the tube is connected to the expandable elastic support layer at and around the periphery of the hole of the expandable elastic support layer.

14. The annular dynamic adherent cell support of claim 13, wherein the first exterior portion comprises an annular shape defining a hole, and wherein a diameter of the hole of the first exterior portion is equal to the diameter of the hole of the expandable elastic support layer, and wherein an outer diameter of the first exterior portion is equal to an outer diameter of the expandable elastic support layer.

15. The annular dynamic adherent cell support of claim 1, wherein the internal passage is separate from the void.

16. The annular dynamic adherent cell support of claim 1, wherein the internal passage is connected to the first exterior portion of the annual support base at a point offset from the aperture extending through the annular dynamic adherent cell support.

* * * * *